US012673211B2

(12) United States Patent
Li et al.

(10) Patent No.: US 12,673,211 B2
(45) Date of Patent: Jul. 7, 2026

(54) BIOSTIMULATOR HEADER ASSEMBLY HAVING ANTENNA

(71) Applicant: Pacesetter, Inc., Sylmar, CA (US)

(72) Inventors: Perry Li, Arcadia, CA (US); Julianna Teixeira, Glendale, CA (US); Souvik Dubey, Canyon Country, CA (US); Kavous Sahabi, Winnetka, CA (US); Davi Rodrigues, Granada Hills, CA (US); Arees Garabed, North Hills, CA (US)

(73) Assignee: Pacesetter, Inc., Sylmar, CA (US)

( * ) Notice: Subject to any disclaimer, the term of this patent is extended or adjusted under 35 U.S.C. 154(b) by 295 days.

(21) Appl. No.: 18/206,980

(22) Filed: Jun. 7, 2023

(65) Prior Publication Data

US 2023/0398364 A1     Dec. 14, 2023

Related U.S. Application Data

(60) Provisional application No. 63/460,273, filed on Apr. 18, 2023, provisional application No. 63/350,762, filed on Jun. 9, 2022.

(51) Int. Cl.
*A61N 1/372*          (2006.01)
*A61N 1/375*          (2006.01)
(Continued)

(52) U.S. Cl.
CPC ..... *A61N 1/37229* (2013.01); *A61N 1/37518* (2017.08); *A61N 1/3756* (2013.01); *H01Q 1/2291* (2013.01); *H01Q 7/00* (2013.01)

(58) Field of Classification Search
CPC ............ A61N 1/37229; A61N 1/37518; A61N 1/3756; H01Q 1/2291; H01Q 7/00
See application file for complete search history.

(56) References Cited

U.S. PATENT DOCUMENTS 5,552,759 A * 9/1996 Stoyka ............... G08B 13/1472
                                                         340/426.33
6,251,128 B1 * 6/2001 Knopp ............... A61B 18/1492
                                                         607/101

(Continued)

OTHER PUBLICATIONS

PCT Invitation to Pay Additional Fees from related PCT Application No. PCT/IB2023/055950, mailed on Sep. 29, 2023 (13 pages).
(Continued)

*Primary Examiner* — Thien M Le
(74) *Attorney, Agent, or Firm* — WOMBLE BOND DICKINSON (US) LLP

(57)                ABSTRACT

A biostimulator, such as a leadless cardiac pacemaker, has a header assembly that includes an antenna. A header assembly includes an antenna cap having an antenna loop embedded in a cap body. The cap body includes a dielectric material, and the antenna loop extends about a central channel of the cap body. The central channel extends along a longitudinal axis over a cap length, and the cap body has a cap width transverse to the longitudinal axis. The cap body has an aspect ratio of the cap width to the cap length greater than 1. A header assembly includes an antenna loop of the antenna encased in a header body of the header assembly. The header assembly includes a fixation element. A proximal end of the fixation element is encased in the header body. Other embodiments are also described and claimed.

12 Claims, 21 Drawing Sheets

(51) Int. Cl.
　　*H01Q 1/22*　　　　(2006.01)
　　*H01Q 7/00*　　　　(2006.01)

(56) References Cited

U.S. PATENT DOCUMENTS

| | | | | |
|---|---|---|---|---|
| 6,471,830 | B1 * | 10/2002 | Moslehi ................ | C23C 14/358 |
| | | | | 204/192.12 |
| 2004/0169114 | A1 * | 9/2004 | Dierkes ................. | H01Q 1/125 |
| | | | | 248/165 |
| 2008/0180216 | A1 * | 7/2008 | Choi ...................... | H01Q 1/362 |
| | | | | 343/895 |
| 2012/0269522 | A1 * | 10/2012 | Kagaya ................. | H05K 1/025 |
| | | | | 333/204 |
| 2014/0076505 | A1 * | 3/2014 | Mullet .................... | A47H 1/02 |
| | | | | 160/121.1 |
| 2015/0096167 | A1 | 4/2015 | Zhao et al. | |
| 2015/0107788 | A1 * | 4/2015 | Mullet ................. | A47H 5/0325 |
| | | | | 160/405 |
| 2016/0361550 | A1 | 12/2016 | Landherr et al. | |
| 2018/0039878 | A1 * | 2/2018 | Akamatsu ............ | G06K 19/077 |
| 2021/0152921 | A1 * | 5/2021 | Silva .................... | H04R 1/1041 |
| 2021/0187310 | A1 | 6/2021 | Zhang et al. | |
| 2021/0260389 | A1 | 8/2021 | Dubey et al. | |
| 2021/0327860 | A1 * | 10/2021 | Libsch ................. | H01L 25/167 |

OTHER PUBLICATIONS

PCT International Search Report and Written Opinion from related PCT Application No. PCT/IB2023/055950, mailed on Nov. 22, 2023 (20 pages).

PCT International Preliminary Report on Patentability from related PCT Application No. PCT/IB2023/055950, mailed on Dec. 19, 2024, 14 pages.

* cited by examiner

BIOSTIMULATOR HEADER ASSEMBLY HAVING ANTENNA

This application claims the benefit of priority of U.S. Provisional Patent Application No. 63/350,762, filed on Jun. 9, 2022, titled "Biostimulator Having Antenna Cap," and U.S. Provisional Patent Application No. 63/460,273, filed on Apr. 18, 2023, titled "Biostimulator Header Assembly Having Antenna," which are incorporated herein by reference in their entirety to provide continuity of disclosure.

BACKGROUND

Field

The present disclosure relates to biostimulators. More specifically, the present disclosure relates to leadless biostimulators having header assemblies.

Background Information

Cardiac pacing by an artificial pacemaker provides an electrical stimulation to the heart when its own natural pacemaker and/or conduction system fails to provide synchronized atrial and ventricular contractions at rates and intervals sufficient for a patient's health. Such antibradycardial pacing provides relief from symptoms and even life support for hundreds of thousands of patients. Cardiac pacing may also provide electrical overdrive stimulation to suppress or convert tachyarrhythmias, again supplying relief from symptoms and preventing or terminating arrhythmias that could lead to sudden cardiac death.

Cardiac pacing by currently available or conventional pacemakers is usually performed by a pulse generator implanted subcutaneously or sub-muscularly in or near a patient's pectoral region. Pulse generator parameters are usually interrogated and modified by a programming device outside the body, via a loosely-coupled transformer with one inductance within the body and another outside, or via electromagnetic radiation with one antenna within the body and another outside. The generator usually connects to the proximal end of one or more implanted leads, the distal end of which contains one or more electrodes for positioning adjacent to the inside or outside wall of a cardiac chamber. The leads have an insulated electrical conductor or conductors for connecting the pulse generator to electrodes in the heart.

Conventional pacemakers have several drawbacks, including complex connections between the leads and the pulse generator, and a risk of infection and morbidity due to the separate leads and pulse generator components. Self-contained and self-sustainable biostimulators, or so-called leadless biostimulators, have been developed to address such drawbacks. A leadless biostimulator has no connections between the pulse generator and a lead. Furthermore, the leadless biostimulator can be attached to tissue within a dynamic environment, e.g., within a chamber of a beating heart, with reduced likelihood of infection. Accordingly, leadless biostimulator technology represents the latest advancement in pacemaker technology. The leadless biostimulator can interact with the tissue using a header assembly, which typically includes a fixation mechanism to attach to the tissue and an electrical feedthrough to deliver electrical impulses from the pulse generator to the tissue.

SUMMARY

Some existing leadless biostimulators communicate with an external device, such as a programmer, using conducted communications. More particularly, the leadless biostimulator can send a signal through tissue of a patient to an electrode of the external device that is in contact with the patient's skin. Thus, the tissue serves as a communication channel between the external device and the biostimulator. Tissue-conducted communications may, however, suffer from limited data exchange, sensitivity to external signaling, and an inability to interrogate the leadless biostimulator at a distance.

Leadless biostimulators could benefit from the ability to wirelessly communicate data, such as performance information, from the implanted biostimulator to an external device. To enable such communication, an antenna can be integrated into the leadless biostimulator. The antenna could be used to communicate Bluetooth Low Energy (BLE) signals. It may be undesirable, however, to integrate the antenna if it requires an increase in a size of the biostimulator. For example, if the antenna requires an increase to the size of a biostimulator housing, it could negatively impact device implantation and/or performance. Compactness of implantable devices is paramount, and thus, there is a need to integrate an antenna within a biostimulator without changing the form factor of the biostimulator.

A biostimulator having an antenna to wirelessly communicate signals is provided. The antenna is integrated into a header assembly. For example, the antenna can be embedded in an antenna cap or encased in a header body of the header assembly. Accordingly, the antenna may not require enlargement of the biostimulator form factor, and may be compact and able to communicate signals from within a patient to a remotely located external device.

In an embodiment, a header assembly incorporates an antenna cap. The antenna cap can include a cap body formed from the dielectric material. The dielectric material may be, for example, a ceramic. In an embodiment, the ceramic is a Low Temperature Co-fired Ceramic (LTCC) having a dielectric constant in a range of 8-11, e.g., 9. An antenna can be at least partly disposed within the cap body. In an embodiment, the antenna includes an antenna loop embedded in the cap body. The cap body can have a central channel to receive an electrode of the biostimulator, and the antenna loop can extend about the central channel and, thus, the electrode. The dielectric material of the cap body can therefore isolate the antenna loop from conductive components of the biostimulator, such as the electrode. The dielectric material can also reduce parasitic coupling and unwanted noise between conductive components of the biostimulator and the antenna to allow for effective wireless communication of signals, e.g., BLE signals, from the biostimulator to an external device.

The antenna cap can be compact. In an embodiment, an aspect ratio of a cap width of the cap body to a cap length of the cap body is greater than 1. Accordingly, the antenna cap can have a flattened annular shape that integrates within the header assembly in a compact form factor. The form factor may also be atraumatic. For example, a distal cap end of the antenna cap can be flattened and/or rounded to ensure that the target tissue is not injured by the antenna cap when the biostimulator is implanted at a target tissue site.

In an embodiment, a header assembly for a biostimulator includes an antenna, a fixation element, and a header body. The antenna includes an antenna loop extending about a longitudinal axis. The fixation element extends helically about the longitudinal axis from a proximal end to a distal tip. The header body includes an insulative material encasing the antenna loop and the proximal end of the fixation element.

In an embodiment, a biostimulator includes the header assembly. The header assembly is mounted on a housing having an electronics compartment containing electronic circuitry. An electrical feedthrough electrically connects to the electronic circuitry and extends through the housing. The antenna of the header assembly includes an antenna loop electrically connected to the electrical feedthrough.

A method of manufacturing the header assembly is provided. The method includes molding one or more insulative materials into a first portion of a header body around the antenna. The method includes locating a proximal end of the fixation element adjacent to the antenna. The method includes molding the one or more insulative materials into a second portion of the header body around the proximal end of the fixation element.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
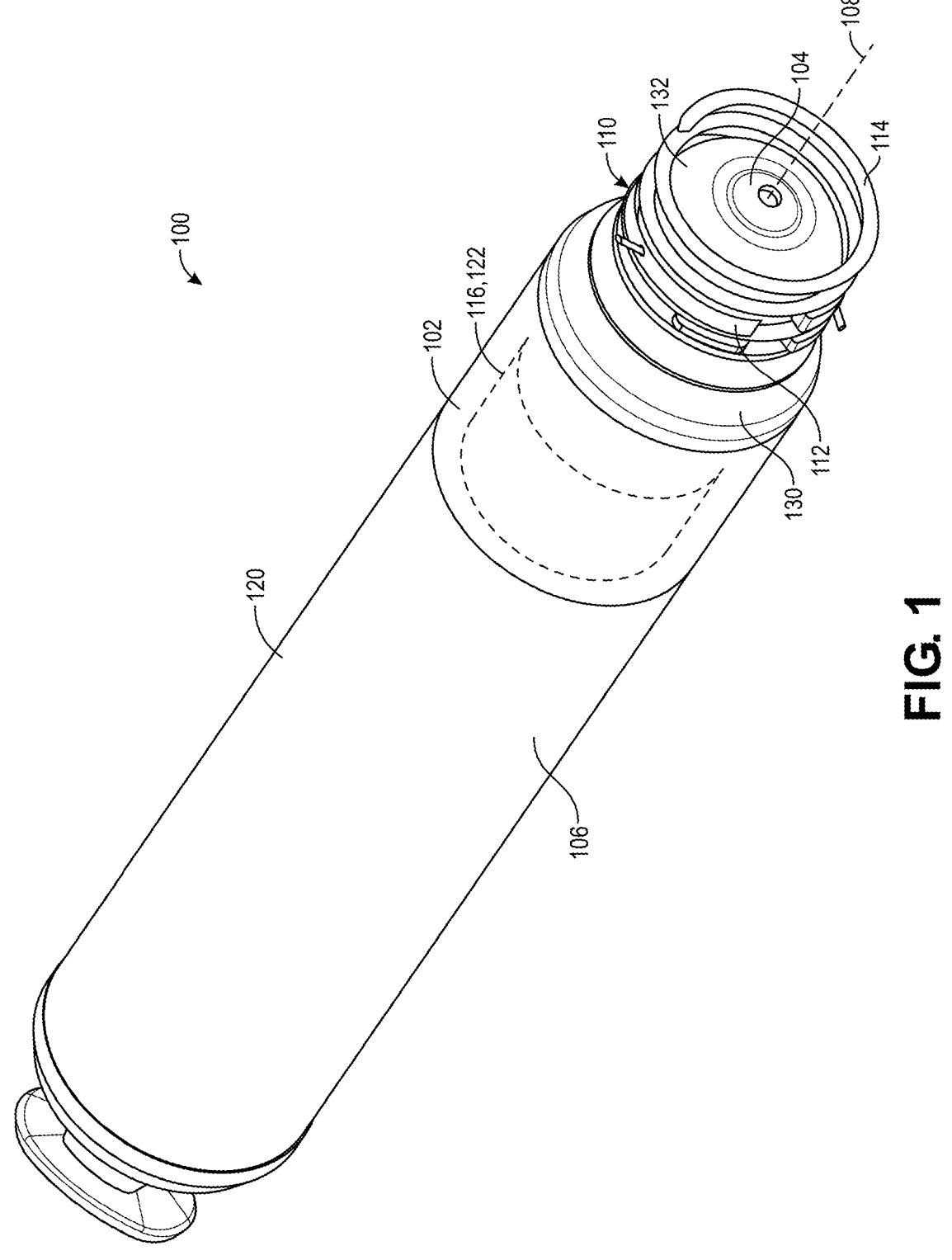
FIG. 1 is a perspective view of a biostimulator, in accordance with an embodiment.

Embodiments describe a biostimulator, e.g., a leadless pacemaker, having a header assembly that includes an antenna. The biostimulator may be used to pace cardiac tissue. Alternatively, the biostimulator may be used in other applications, such as deep brain stimulation. Thus, reference to the biostimulator as being a leadless cardiac pacemaker is not limiting.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

The use of relative terms throughout the description may denote a relative position or direction. For example, "distal" may indicate a first direction along a longitudinal axis of a biostimulator. Similarly, "proximal" may indicate a second direction opposite to the first direction. Such terms are provided to establish relative frames of reference, however, and are not intended to limit the use or orientation of a biostimulator to a specific configuration described in the various embodiments below.

In an aspect, a biostimulator such as a leadless cardiac pacemaker is provided. The biostimulator includes an antenna integrated into a header assembly. More particularly, the antenna can be integrated into an antenna cap that assembles to a helix mount of the header assembly. For example, an antenna loop of the antenna can be embedded within a cap body formed from a dielectric material. The antenna cap can have a low profile, and thus, may be incorporated into the header assembly without increasing a form factor of the biostimulator. The cap body can insulate the antenna from adjacent conductive components, such as a fixation element mounted on the helix mount, while allowing wireless signals to be transmitted and received through the antenna loop.

In an aspect, a biostimulator includes an antenna integrated into a header assembly. More particularly, the antenna can be integrated into a header body that includes insulative material encasing the antenna. The header body may also encase a proximal end of a fixation element. For example, the fixation element can extend helically from within the header body to a distal tip, distal to the header body. The header body can secure and insulate the antenna and fixation element. In an embodiment, the fixation element is electrically connected to an antenna loop of the antenna, such that the antenna has a loop portion and a helical portion. Accordingly, the two-part antenna can have substantial surface area for wireless signal capture.

Referring to FIG. 1, a perspective view of a biostimulator is shown in accordance with an embodiment. A biostimulator 100 can be a leadless biostimulator, e.g., a leadless cardiac pacemaker. The biostimulator 100 can include an electrode 104 at a distal end of the device, and a proximal electrode 106 proximal to the electrode 104. The electrodes can be integral to a housing 102, or connected to the housing, e.g., at a distance of less than several centimeters from the housing 102. The housing 102 can contain an energy source to provide power to the pacing electrodes. The energy source can be a battery 120, such as a lithium carbon monofluoride (CFx) cell, or a hybrid battery, such as a combined CFx and silver vanadium oxide (SVO/CFx) mixed-chemistry cell. Similarly, the energy source can be an ultracapacitor. In an embodiment, the energy source can be an energy harvesting device, such as a piezoelectric device that converts mechanical strain into electrical current or voltage. The energy source can also be an ultrasound transmitter that uses ultrasound technology to transfer energy from an ultrasound subcutaneous pulse generator to a receiver-electrode implanted on an endocardial wall.

The biostimulator 100 can have a longitudinal axis 108. The longitudinal axis 108 can be an axis of symmetry, along which several biostimulator components are disposed. For example, a header assembly 110 can be mounted on a distal end of the housing 102 along the longitudinal axis 108. The header assembly 110 can include an electrical feedthrough subassembly including an electrical feedthrough (not shown) and the electrode 104, e.g., a pacing tip. The header assembly 110 can also include a fixation subassembly. The fixation subassembly can include a helix mount 112. The helix mount 112 can be mounted on the electrical feedthrough subassembly around the longitudinal axis 108. In an embodiment, the fixation subassembly includes a fixation element 114 mounted on the helix mount 112 along the longitudinal axis 108. The fixation element 114 can include a structure to engage and affix to tissue. For example, the fixation element 114 may include a helical or non-helical fixation mechanism. Helical fixation mechanisms are shown in the figures and may include a spiral-wound wire to thread into tissue. Non-helical fixation mechanisms may, for example, include one or more tines to extend longitudinally into and laterally outward within tissue. Other fixation mechanisms include barbs, hooks, etc. In any case, the assembled components of the biostimulator 100 can provide a distal region that attaches to a target tissue, e.g., via engagement of the fixation element 114 with the target tissue. The distal region can deliver a pacing impulse to the target tissue, e.g., via the distal electrode 104 that is held against the target tissue.

The housing 102 can contain an electronics compartment 116. More particularly, the housing 102 can have a housing wall, e.g., a cylindrical wall, laterally surrounding the electronics compartment 116. The housing wall can include a conductive, biocompatible, inert, and anodically safe material such as titanium, 316L stainless steel, or other similar materials, to laterally enclose the electronics compartment 116. The electronics compartment 116 can be axially enclosed at a proximal end by the battery 120. More particularly, a distal surface or face of the battery 120 can define the proximal end of the electronics compartment 116. The electronics compartment 116 can be axially enclosed at a distal end by the header assembly 110. More particularly, a proximal surface of a feedthrough subassembly of the header assembly 110 can define the distal end of the electronics compartment 116. The housing 102 can be attached, e.g., welded, to the header assembly 110 and the battery 120. Accordingly, the electronics compartment 116 can be contained between the battery 120, an inner surface of the housing 102, and the header assembly 110.

In an embodiment, electronic circuitry is contained within the electronics compartment 116. The electronic circuitry can include an electronic component 122. For example, the electronic circuitry can include one or more passive electronic components, e.g., capacitors, and one or more active electronic components, e.g., processors. The electronic components 122 within the electronic compartment 116 can be interconnected by electrical traces, vias, or other electrical connectors.

The biostimulator components can form a hermetic enclosure around the electronic circuitry. For example, the battery 120, housing 102, and header assembly 110 can be welded along mating seams at the proximal and distal ends of the housing 102 to hermetically seal the electronics compartment 116. A feedthrough subassembly (FIG. 6) can provide an isolated electrical path from the electronic component 122, which is hermetically sealed within the electronics compartment 116, to the electrode 104. More particularly, in an embodiment, the feedthrough subassembly transmits afferent and efferent signals between the electronic circuitry and a target tissue.

In an embodiment, the header assembly 110 for the biostimulator 100 includes a flange 130, the helix mount 112, and an antenna cap 132. The flange 130, as described further below, can be mounted on the housing 102 to enclose the electronics compartment 116. The helix mount 112 may be mounted on the flange 130. The helix mount 112 can receive the fixation element 114. The antenna cap 132 can, in turn, be mounted on the helix mount 112. The antenna cap 132 can be integrated with the helix mount 112 as a component of the header assembly 110 to provide a low-profile external envelope that is compact and atraumatic to tissue. More particularly, the antenna cap 132 can have a form factor that fits within a space between the fixation element 114 and the electrode 104. As described below, a distal end of the antenna cap 132 can be rounded and/or smooth to allow the antenna cap 132 to be drawn against tissue without injuring the tissue. Accordingly, the antenna cap 132 is a header assembly component that provides an antenna module at a distal end of the biostimulator 100, in a compact and atraumatic form factor.

Figure 2:
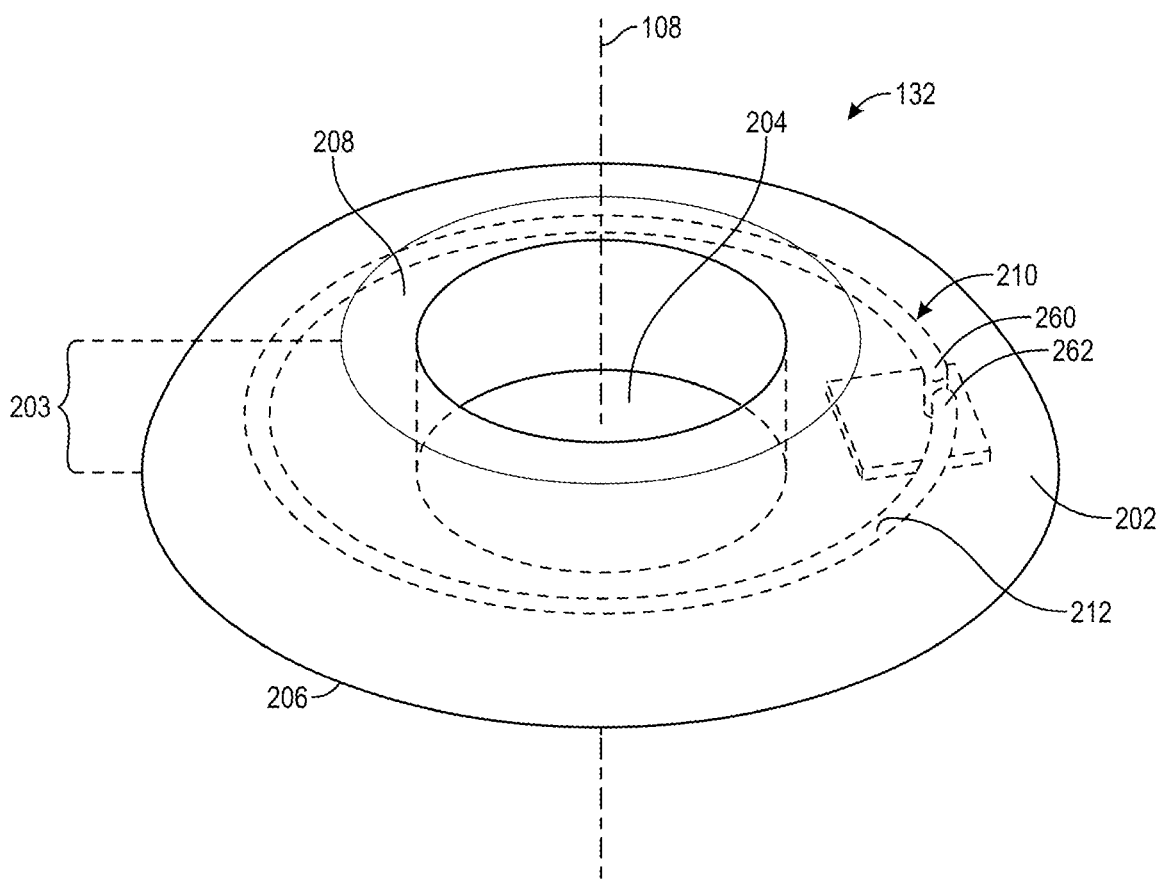
FIG. 2 is a perspective view of an antenna cap, in accordance with an embodiment.

Referring to FIG. 2, a perspective view of an antenna cap is shown in accordance with an embodiment. The antenna cap 132 includes a cap body 202 shaped to integrate with the header assembly 110. More particularly, the cap body 202 can have a central channel 204 extending along the longitudinal axis 108 over a cap length 203 between a proximal cap end 206 and a distal cap end 208. As described below, the cap body 202 can have a rounded shape that is atraumatic. Furthermore, the central channel 204 can be sized and shaped to receive and conform to an outer diameter of the electrode 104. Accordingly, the distal cap end 208 and the distal end of the electrode 104 can provide a distal surface for the biostimulator 100 that presses atraumatically against the target tissue.

In an embodiment, the antenna cap 132 is formed from a dielectric material. For example, the dielectric material can be a ceramic, an epoxy, or a plastic. Selection of the dielectric material can influence performance of an antenna 210, which is at least partly embedded in the cap body 202. More particularly, the antenna 210 can include an antenna loop 212 that is embedded in the cap body 202, and a dielectric constant of the dielectric material can affect performance of the antenna loop 212. In an embodiment, the dielectric constant is selected to allow the antenna 210 to be smaller than, e.g., a similarly shaped antenna that is not embedded in a dielectric material. More particularly, the dielectric material can have a dielectric constant in a range of 2 to 12. For example, the dielectric material may be a ceramic having a dielectric constant of 9. The dielectric material can enhance antenna performance and allow for miniaturization of the antenna.

The cap body 202 may be formed from any of several ceramic materials having a dielectric constant within the predetermined range. For example, the ceramic material may be selected from a group of ceramic materials, such as Low Temperature Co-fired Ceramics (LTCC). In an embodiment, the ceramic material includes LTCC. The LTCC can be fabricated using a process including a sintering operation having a sintering temperature below 1000 degrees Celsius. The LTCC may include a glass ceramic material, such as glass, calcium zirconate, and/or alumina, for example. By carefully selecting the dielectric material of the antenna module, near-field absorption losses of the antenna 210 may be minimized.

The antenna loop 212, which may be embedded in the dielectric material of the cap body 202, can extend about the central channel 204. For example, the antenna loop 212 can extend partially or entirely around the central channel 204. When formed as a closed loop, the antenna loop 212 can extend entirely around the central channel 204. When formed as an open loop, e.g., a c-shaped loop, the antenna loop 212 can extend only partially around the central channel. In an embodiment, the antenna 210 is a monopole antenna. For example, the antenna loop 212 can include a single loop extending from a first antenna end 260 to a second antenna end 262. The antenna ends can be separated by a gap to form an open loop antenna. Accordingly, the antenna loop 212 may be a metallic trace extending in a circular fashion about the longitudinal axis 108 through the cap body 202. Given that the antenna trace extends around the central channel 204, which may be configured to receive the electrode 104, the antenna loop 212 can encircle the tip electrode 104. A length of the antenna loop 212, e.g., a circumference of the loop, may be sized to provide optimal impedance and a low reflection coefficient.

The antenna loop 212 may be formed in a single layer trace. Alternatively, the antenna 210 can include several antenna loops stacked vertically within the cap body 202, or the single layer trace can extend in a spiral to provide several layers in a single trace. Increasing a trace length of the antenna loop 212 can allow for a dielectric material having a lower dielectric constant to be selected for a same antenna performance.

As shown in FIG. 2, the cap body 202 can have a circular annular shape. The cap body 202 may, however, have a non-circular annular shape. For example, an outer edge of the cap body 202 may, rather than being circular, be polygonal, elliptical, etc. The outer edge can have any non-circular shape. In an embodiment, the shape of the outer edge that defines an outer perimeter of the annulus can conform to the envelope encircled by the fixation element 114. For example, the fixation element 114 can be a spiral, and thus, the outer edge can be circular to match the inner profile of the spiral.

Figure 3:
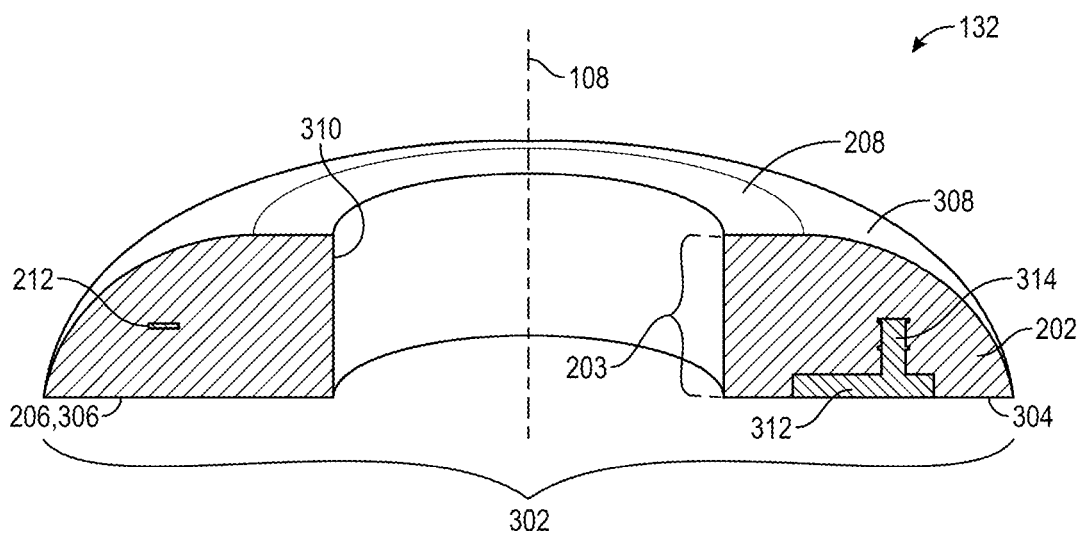
FIG. 3 is a perspective cross-sectional view of an antenna cap, in accordance with an embodiment.

Referring to FIG. 3, a perspective cross-sectional view of an antenna cap is shown in accordance with an embodiment. The annular antenna cap 132 can have the cap length 203 between the proximal cap end 206 and the distal cap end 208 in a longitudinal direction along the longitudinal axis 108. A cap width 302 of the cap body 202 can be a dimension transverse to the longitudinal axis 108. More particularly, the cap width 302 can be measured in a direction orthogonal to the direction of the cap length 203. The cap width 302 can be an outer dimension of an outer edge 304 of the cap body 202, e.g., a diameter of the annulus. For example, the outer dimension can be a width of a proximal cap face 306 measured in the transverse direction at the proximal cap end 206.

The proximal cap face 306 may be a flat face, as shown in FIG. 3. Alternatively, the proximal cap face 306 may have curvature. A distal cap face 308 can extend from the outer edge 304 to the distal cap end 208, which may be a flattened distal end of the antenna cap 132. The distal cap face 308 can be a curved distal cap face 308. Like the proximal cap face 306, all or a portion of the distal cap face 308 can be flat, such as a portion of the distal cap face 308 radiating from a sidewall 310 surrounding the central channel 204 to a curved portion of the distal cap face 308. In any case, the outer edge 304 can be a location at which the proximal cap face 306 meets the distal cap face 308 of the antenna cap 132.

The cap body 202 can have an aspect ratio defined by the cap length 203 and the cap width 302. More particularly, a ratio of the cap width 302 to the cap length 203 can be the aspect ratio of the cap body 202. As described above, the form factor of the antenna cap 132 can be compact, and the antenna cap 132 can fit within the inner envelope defined by the fixation element 114. Accordingly, in an embodiment, the aspect ratio of the cap body 202 is greater than 1. More particularly, the cap width 302 is greater than the cap length 203, and the antenna cap 132 has a flattened annular shape.

An alternative aspect ratio can compare a cross-sectional height to a cross-sectional width of the cap body 202. The cross-sectional height of the cap body 202 can be the cap length 203, e.g., a vertical height of the sidewall 310. The sidewall 310 can be flat (cylindrical) and extend around the longitudinal axis 108. The cross-sectional width of the cap body 202 can be a distance extending from the sidewall 310 to the outer edge 304 along the proximal cap face 306. The proximal cap face 306 may be flat and extend horizontally. The aspect ratio of the cross-sectional width to the cross-sectional height may be greater than one. More particularly, the cross-sectional width can be greater than the cross-sectional height.

The antenna loop 212 can be embedded within the cap body 202 such that the cap body 202 surrounds the loop structure. For example, the cross-section of the cap body 202 reveals that the dielectric material surrounds the antenna loop 212. In an embodiment, the antenna loop 212 is vertically centered between the distal cap end 208 and the proximal cap end 206. The antenna loop 212 may be biased toward the distal cap face 308 in the transverse direction. More particularly, the antenna loop 212 may have a radius from the longitudinal axis 108 such that the loop structure is nearer to the distal cap face 308 than to the sidewall 310.

In an embodiment, the antenna cap 132 includes a contact pad 312 electrically connected to the antenna loop 212. More particularly, a lead 314 can electrically connect the contact pad 312 to the antenna loop 212. The contact pad 312 may be exposed on the proximal cap face 306 of the cap body 202. Accordingly, an electrical signal can be applied to the contact pad 312 from an external structure. The lead 314 can extend vertically from the contact pad 312 to the antenna loop 212. For example, the lead 314 may be formed as a via extending through the cap body 202 from the contact pad 312 at the proximal cap end 206 to the antenna loop 212 within the cap body 202. The antenna structures, e.g., the antenna loop 212, the lead, and the contact pad 312, may be formed from electrically conductive and biocompatible materials. For example, the antenna components may be formed from platinum, titanium, stainless steel, etc. Thus, electrical signals can be communicated through the lead 314 between the contact pad 312 and the antenna loop 212 while the antenna cap 132 is implanted in a patient.

Figure 4:
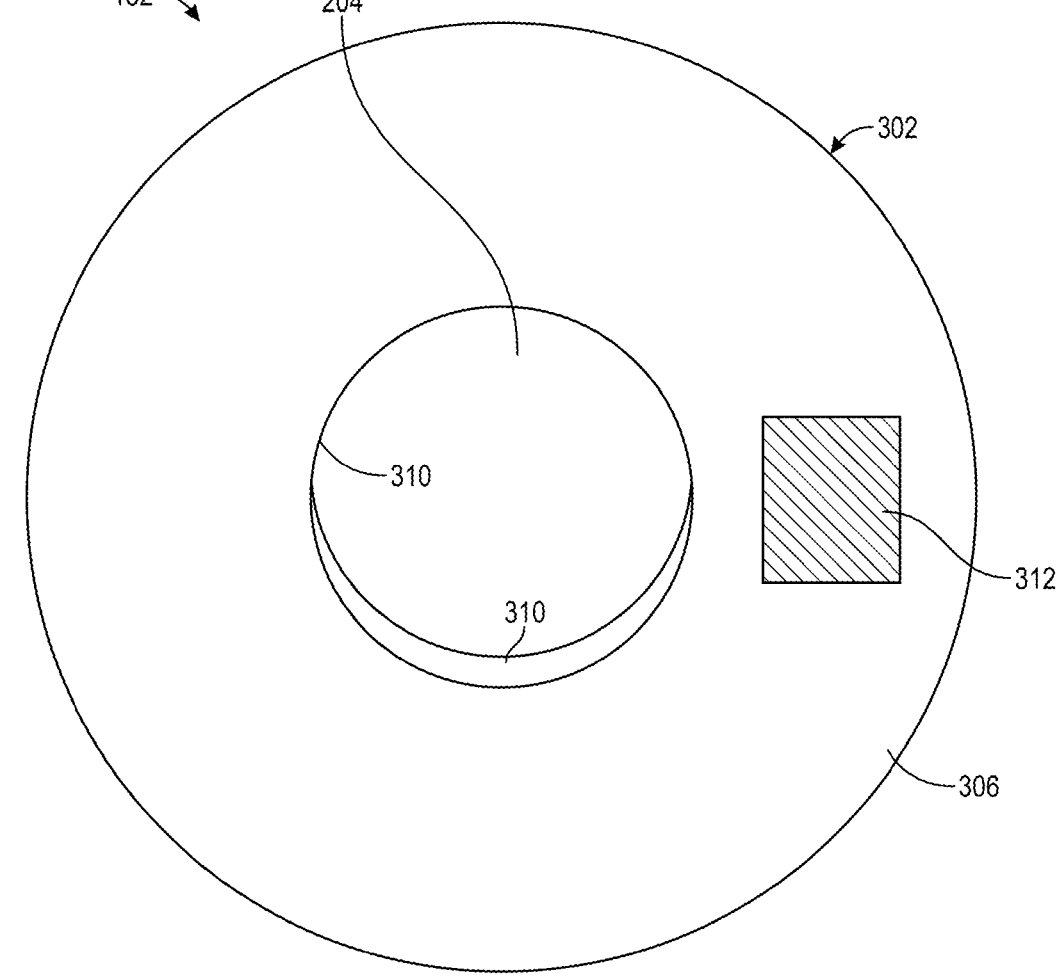
FIG. 4 is a perspective bottom view of an antenna cap, in accordance with an embodiment.

Referring to FIG. 4, a perspective bottom view of an antenna cap is shown in accordance with an embodiment. The contact pad 312 can be exposed on the proximal cap face 306 to allow the pad to be placed in contact with an external conductor, such as a pin. More particularly, as described below, the contact pad 312 can be used for connecting the antenna module to an RF feedthrough pin. A size and shape of the contact pad 312 may be selected based on a bond that is to be formed between the contact pad 312 and the external conductor. The size and shape of the contact pad 312 may also be selected to provide an impedance of the antenna 210 that achieves optimal impedance matching in the human tissue after implantation. The illustrated example of the contact pad 312 has a rectangular shape; however, other pad shapes may be used.

Figure 5:
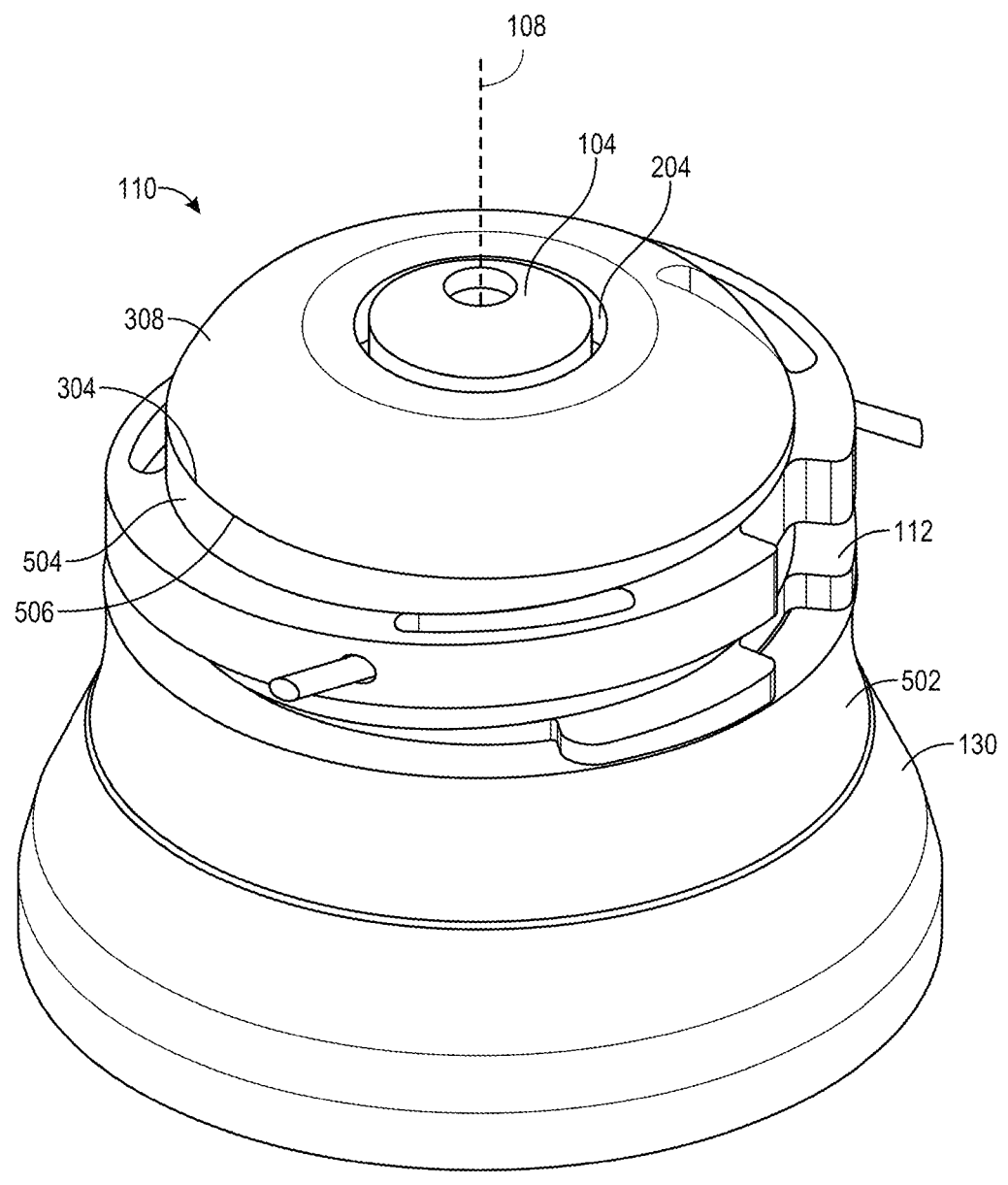
FIG. 5 is a perspective view of a header assembly of a biostimulator, in accordance with an embodiment.

Referring to FIG. 5, a perspective view of a header assembly of a biostimulator is shown in accordance with an embodiment. As described above, the header assembly 110 for the biostimulator 100 includes the helix mount 112 mounted on the flange 130. For example, the helix mount 112 may be screwed on to a receiving thread of the flange 130 (FIG. 6) and the components can be bonded together by an adhesive joint 502.

The antenna cap 132 can be mounted on the helix mount 112. Antenna cap 132 can be manufactured separately from the helix mount 112 and then mounted on the helix mount 112 using adhesive, mechanical, or other attachment mechanisms. Accordingly, the modular antenna 210 can be provided as a subcomponent that may be assembled into header assemblies of various biostimulator designs.

Figure 6:
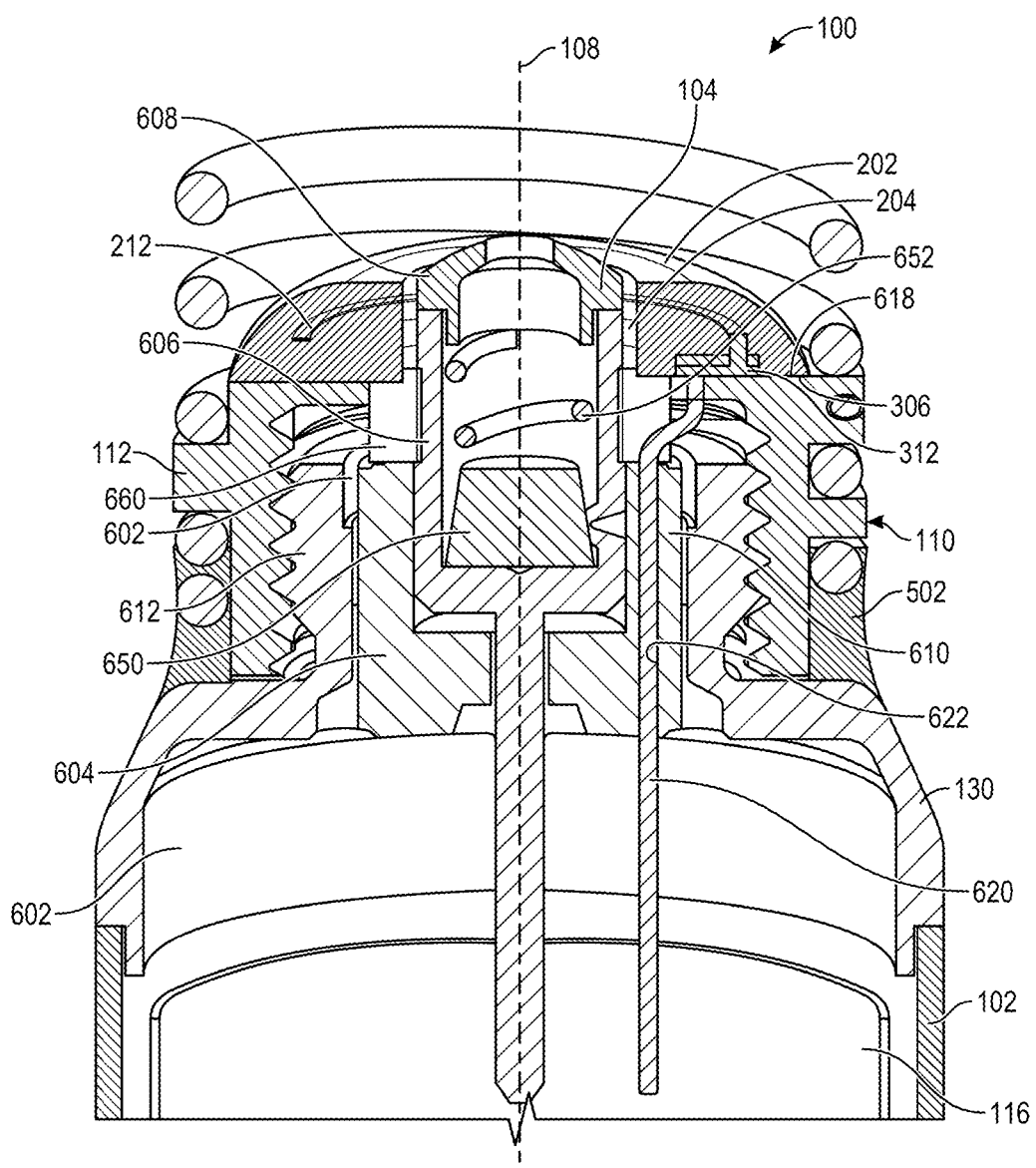
FIG. 6 is a cross-sectional view of a header assembly of a biostimulator, in accordance with an embodiment.

The helix mount 112 may include a mount wall 504 facing radially outward, away from the longitudinal axis 108. The mount wall 504 can include a helical ridge to receive the fixation element 114 (FIG. 6). In an embodiment, the mount wall 504 has a distal edge 506. The outer edge 304 of the cap body 202 coincides with the distal edge 506 of the helix mount 112. For example, the outer edge 304 and the distal edge 506 can both be circular and have a same diameter. Accordingly, the matching dimensions of the cap body 202 and the helix mount 112 can provide a smooth transition between the distal cap face 308 and the mount wall 504.

Referring to FIG. 6, a cross-sectional view of a header assembly of a biostimulator is shown in accordance with an embodiment. The header assembly 110 can include an electrical feedthrough subassembly that is a multifunction component. Unlike a traditional pacemaker where the electrical feedthrough is separated from the pacing site by a lead and functions solely to transfer power to the lead, the distal electrode 104 of the electrical feedthrough subassembly of the biostimulator 100 may be in direct contact with the stimulation site and used to deliver impulses to the tissue. Additionally, the electrical feedthrough subassembly can not only serve as the electrical pass-through from a hermetic package to a surrounding environment, but may also serve other functions, such as providing a housing for a steroid or other filler 650, or providing direct tissue interaction.

The feedthrough subassembly can include several components having respective functions. The flange 130 of the subassembly can be connected to the housing 102 of the biostimulator 100. For example, the flange 130 can be mounted on and bonded to the housing 102 by a weld. The flange 130 can include a flange channel 602 extending along the longitudinal axis 108. The flange channel 602 may be aligned, for example, with the central channel 204 of the cap body 202 along the longitudinal axis 108.

The subassembly can include an insulator 604 to electrically isolate the flange 130 from electrical components passing from the hermetic enclosure of the biostimulator 100 to the surrounding environment. For example, the insulator 604 can include and/or be formed from a ceramic material that insulates the flange 130 from the electrode 104. The electrode 104 can connect a pulse generator of the electronic circuitry to a pacing tip. The electrode 104 can be within the flange channel 602, and the insulator 604 may also be within the flange channel 602 between the electrode 104 and both the flange 130 and the helix mount 112. The flange 130, the insulator 604, and the electrode 104 can be connected by a brazed joint that hermetically seals the components and fluidically isolates a distal region of the flange channel 602 from a proximal region of the flange channel 602 that opens to the electronics compartment 116.

In certain implementations, the electrical feedthrough subassembly can be an unfiltered assembly. More particularly, the configuration of the electrical feedthrough subassembly can include an active component, e.g., the distal electrode 104, isolated from a ground component (e.g., the flange 130) by the insulator 604. The electrode 104 may include the pacing tip, which can include an electrode body 606 and/or an electrode tip 608. In implementations of the present disclosure, the electrode tip 608 may be mounted on the electrode body 606, e.g., on a distal end of the electrode body 606, as illustrated in FIG. 6. The electrode body 606 and electrode tip 608 can be welded together.

The electrode 104 can include a monolithic electrode body 606. For example, the monolithic electrode body 606 can have several distinct portions that are integrally formed with each other. In one implementation, the electrode body 606 includes a cup and a pin that are integrally formed such that the electrode body 606 is monolithic, or, in other words, has a unitary or single-piece construction. The pin can conduct pacing signals from electronic circuitry within the electronics compartment 116. The signals can be conducted to the cup and transmit distally through the electrode tip 608 to the target tissue.

The insulator 604 can surround a portion of the electrode body 606. More particularly, the insulator 604 can include an insulator wall 610 that contains and separates the conductive electrode body 606 from a flange wall 612 of the flange 130. Both the electrode body 606 and the flange wall 612 can be conductive. By contrast, the insulator 604 can be formed from an alumina ceramic or other insulating material. Accordingly, the insulator 604 can be located between the electrode body 606 and the flange wall 612 to electrically insulate the distal electrode 104 from the flange 130. The flange wall 612 can include a thread, e.g., an external thread on an outer surface, which may form a threaded connection between the electrical feedthrough subassembly and the helix mount 112 of the header assembly 110. The helix mount 112 may alternatively be bonded, press-fit, or otherwise coupled to the flange 130.

The proximal cap face 306 of the antenna cap 132 can be apposed to a distal mount face 618 of the helix mount 112 when the antenna cap 132 is mounted on the helix mount 112. As described above, the proximal cap face 306 can be flat and, in an embodiment, the distal mount face 618 is similarly shaped, e.g., flat, to conform to the proximal cap face 306. The faces can be bonded or otherwise connected to assemble the antenna module into the header assembly 110.

When the antenna cap 132 is installed on the helix mount 112, the antenna loop 212 can encircle the central channel 204. Furthermore, given that the electrode 104 extends longitudinally through the central channel 204, the antenna loop 212 can encircle the electrode 104. The antenna loop 212 surrounding the electrode 104 can nonetheless be isolated from the electrode 104 and the fixation element 114 by the dielectric material of the cap body 202. More particularly, the dielectric material of the cap body 202 can isolate the antenna loop 212 from other metals of the biostimulator 100, e.g., the fixation element 114, electrode 104, or flange 130. Accordingly, parasitic coupling and unwanted noise between conductive components of the biostimulator 100 and the antenna 210 can be reduced.

Whereas pacing signals can be delivered from electronic circuitry within the electronics compartment 116 through the electrode 104 to the target tissue, communication signals may be delivered from the electronic circuitry to the antenna module through a dedicated electrical path. In an embodiment, the electronic component 122 (not shown) within the electronics compartment 116 can be electrically connected to the antenna 210 through a connector pin 620. The electronic circuitry may be in electrical communication with the electrode pin and/or the connector pin 620 through a socket connector or another electrical connection.

The insulator wall 610 can include a pin channel 622, and the connector pin 620 can extend through the pin channel 622. For example, the pin channel 622 can be a hole or lumen extending vertically through the insulator wall 610, parallel to the longitudinal axis 108. The connector pin 620 can be narrower than the channel, and may be fit through the channel to extend from a proximal pin end within the electronics compartment 116 to a distal pin end distal to the insulator 604. The connector pin 620 can pass through the hole in the insulator 604 such that it remains insulated from adjacent conductive components of the header assembly 110. More particularly, the connector pin 620 can be isolated from the electrode 104 and the flange 130 by the surrounding insulator material.

The distal pin end can be electrically connected to the antenna loop 212. For example, the connector pin 620 can extend from the insulator 604 through a cutout in the helix mount 112 to be placed in contact with the contact pad 312. The distal pin end may be brazed or welded to the contact pad 312, which is in electrical communication with the antenna loop 212 through the lead. Accordingly, the electronic component 122 can communicate Bluetooth Low Energy (BLE) signals through the connector pin 620 and the antenna loop 212 to and from an external device. More particularly, communication circuitry can use the antenna 210 to communicate wirelessly with an external communication device.

In an embodiment, the biostimulator 100, and more particularly the electrical feedthrough subassembly, can include the filler 650, such as a monolithic controlled release device (MCRD). By way of introduction and without limitation, the filler 650 may include a therapeutic material, and can be loaded into the electrode cup. Accordingly, the filler 650 can deliver a specified dose of a therapeutic agent, e.g., a corticosteroid, into target tissue at an implantation site of the biostimulator 100 within a patient. In an embodiment, the filler 650 is retained at a proximal location within an interior cavity of the cup by a retention spring 652. The retention spring 652 can press against a distal end of the filler 650 and a proximal end of the electrode tip 608 to urge the filler 650 away from the electrode tip 608 and reduce the likelihood of the filler 650 clogging a tip hole of the electrode tip 608.

In one implementation, the fixation element 114 includes a helix mounted on the helix mount 112. The fixation element 114 can be suitable for attaching the biostimulator 100 to tissue, such as heart tissue. The helix can extend distally from the helix mount 112 about the longitudinal axis 108. For example, the helix can revolve about the longitudinal axis 108. The helix can include a spiral wire, formed by coiling or cut from a wall of a length of tubing, which extends in a rotational direction around the longitudinal axis 108. For example, the helix can revolve in a right-handed direction about the longitudinal axis 108. In the case of a right-handed spiral direction, the biostimulator 100 can be advanced into contact with a target tissue, and the biostimulator 100 can then be rotated in the right-handed direction to screw the helix into the tissue. The fixation element 114 may alternatively have a left-handed spiral direction to enable the biostimulator 100 to be screwed into the target tissue via left-handed rotation.

In an embodiment, the helix mount 112 may be positioned between the fixation element 114 and the flange 130. The helix mount 112 can electrically isolate the fixation element 114 from the feedthrough subassembly. For example, the helix mount 112 can be formed from an insulating material, such as polyetheretherketone (PEEK) to reduce the likelihood of electrical shorting between the helix and the electrode 104 or the flange 130. The insulating material of the helix mount 112 may also be rigid to mechanically support the fixation element 114 during advancement into the target tissue.

The biostimulator 100 can be implanted in a body region having fluids, e.g., within the blood of a heart chamber, and thus, portions of the biostimulator 100 can be sealed and/or protected against fluid ingress that may compromise functionality of the biostimulator 100. In one implementation, the barrier is provided by a gasket 660. The gasket 660 can be resiliently compressed between the helix mount 112 and the insulator 604. More particularly, the gasket 660 can have an annular body, e.g., an o-ring shape, and the annular body can be resiliently compressed between the helix mount 112 and the insulator 604. The annular body of the gasket 660 can extend around the electrode 104. For example, the annular body can extend circumferentially about the cup. Accordingly, the gasket 660 can fill a gap between a proximal surface of the helix mount 112 and a distal face or surface of the electrical feedthrough subassembly. The compressed gasket 660 can form a seal against the compressing surfaces to fill the gap between the distal electrode 104 and the proximal electrode 106 (e.g., the flange 130). Therefore, the gasket 660 can separate and protect the conductive surfaces of the biostimulator 100 from short circuiting.

Figure 7:
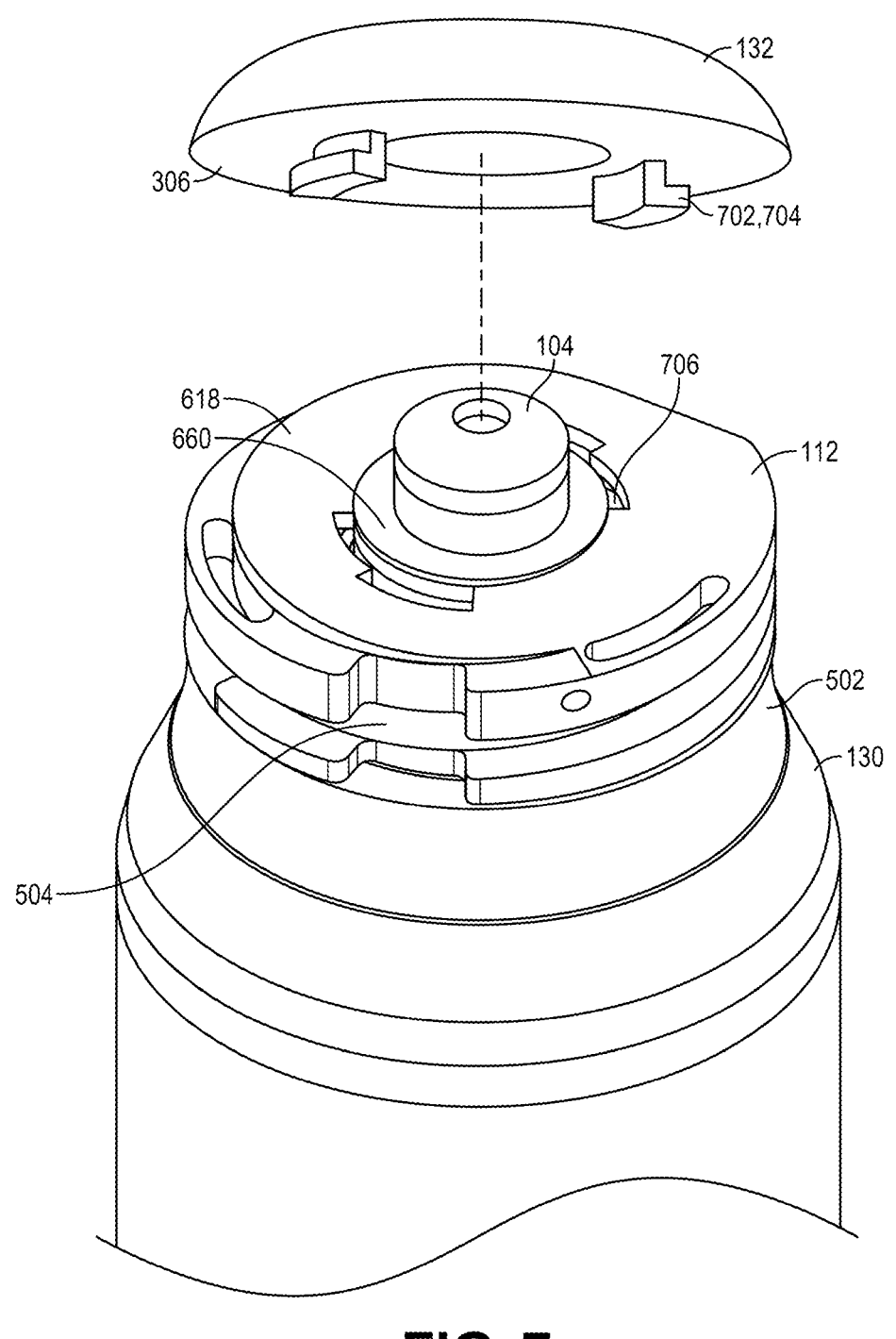
FIG. 7 is a perspective view of an antenna cap dismounted from a header assembly of a biostimulator, in accordance with an embodiment.

Referring to FIG. 7, a perspective view of an antenna cap dismounted from a header assembly of a biostimulator is shown in accordance with an embodiment. The antenna cap 132 can be attached to the helix mount 112 in various manners. In an embodiment, the antenna cap 132 is interlocked with the helix mount 112.

The cap body 202 can include one or more locking features, such as a locking feature 702 extending from the proximal cap face 306. The locking feature 702 can include a key 704. The key 704 can include a vertical prong. A horizontal tab can extend radially from the vertical prong. Accordingly, the key 704 can have an L-shaped cross-sectional profile that includes a horizontal tab.

The helix mount 112 can include a keyway 706 to receive the key 704 of the cap body 202. In an embodiment, the keyway 706 is a slot formed in the distal mount face 618 of the helix mount 112. The slot can include a first segment shaped to receive the horizontal tab, and a second segment shaped to receive the vertical prong. More particularly, the horizontal tab can fit through the first segment by lowering the antenna cap 132 onto the helix mount 112. When the horizontal tab has passed through the slot from a distal side of the distal mount face 618 to a proximal side, e.g., within a cavity surrounded by the mount wall 504, the antenna cap 132 can be rotated to lock the cap into place. Rotating the antenna cap 132 can slide the vertical prong through the second segment of the slot. The horizontal tab can be larger in profile than the second segment, and thus, the horizontal tab can resist dislodgment of the antenna cap 132 from the helix mount 112. Accordingly, the antenna cap 132 can become interlocked with the helix mount 112. Adhesive may be added to the interface between the proximal cap face 306 and the distal mount face 618, e.g., by wicking adhesive into the interface, to further strengthen the connection between the antenna cap 132 and the helix mount 112.

Figure 8:
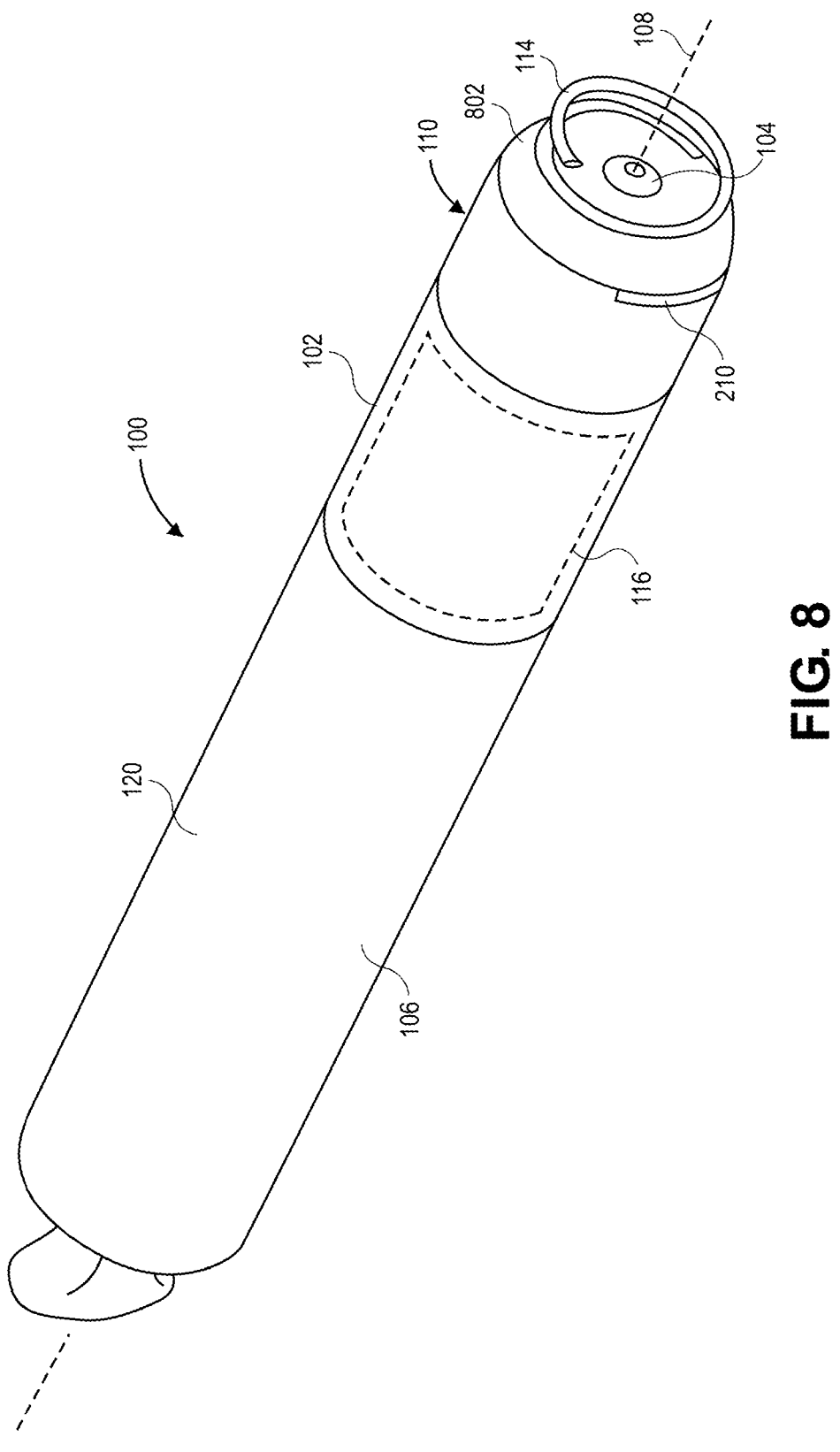
FIG. 8 is a perspective view of a biostimulator, in accordance with an embodiment.

Referring to FIG. 8, a perspective view of a biostimulator is shown in accordance with an embodiment. The biostimulator 100 can be a leadless biostimulator, e.g., a leadless cardiac pacemaker, and may include components described above. For example, the biostimulator 100 can include the housing 102 having the electronics compartment 116 containing electronic circuitry, such as the electronic component 122. The biostimulator 100 may also include the electrodes described above, e.g., electrodes 104, 106, the battery 120, etc.

The header assembly 110 can be mounted on a distal end of the housing 102 along the longitudinal axis 108. The header assembly 110 can include electrical circuitry to connect to the electronic circuitry within the electronics compartment 116. For example, as described below, the electrode 104 can connect to an electrical feedthrough (FIG. 9) to communicate pacing signals. Similarly, an antenna 210 of the header assembly 110 can connect to the electrical feedthrough to relay wireless communication signals.

The header assembly 110 can include the fixation element 114. In an embodiment, the header assembly 110 does not include the helix mount 112 described above. Instead, the fixation element 114 can be secured to the housing 102 by a header body 802. More particularly, the header body 802 can attach to the housing 102, and may encase at least a portion of the fixation element 114 to secure the fixation element 114 to the housing 102.

As described above, the header assembly 110 provides a low-profile external envelope that is compact and atraumatic to tissue. For example, the distal end of the header body 802 can be rounded and/or smooth to allow the header body and the electrode 104 to be drawn against tissue without injuring the tissue. The header body 802 can secure the fixation element 114 that engages the tissue to draw the electrode 104 against the tissue. Additionally, the header body 802 of the header assembly 110 can contain and secure the antenna 210 to provide an antenna module to facilitate wireless communication of data.

Figure 9:
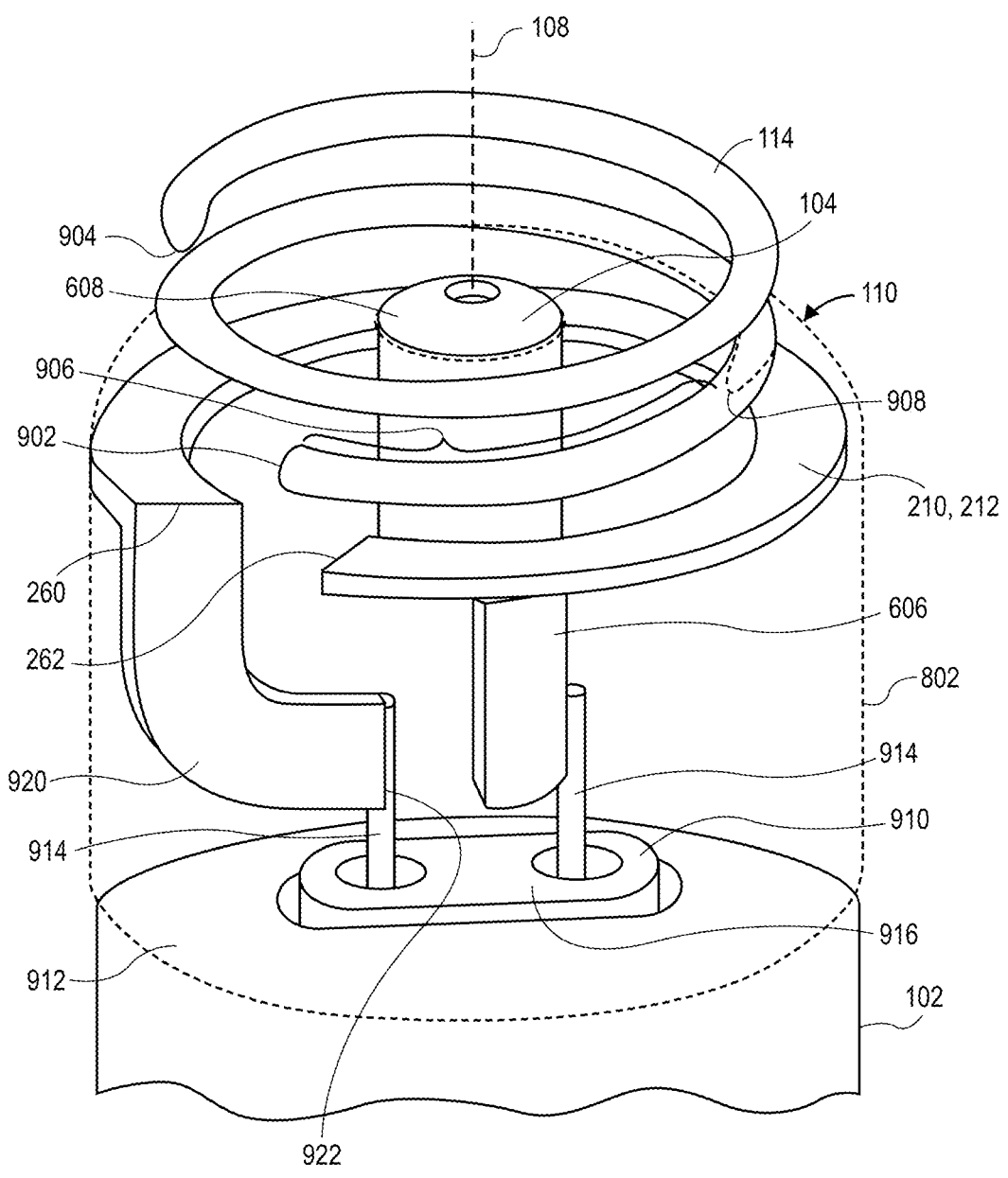
FIG. 9 is a perspective view of a header assembly, in accordance with an embodiment.

Referring to FIG. 9, a perspective view of a header assembly is shown in accordance with an embodiment. The header body 802 is rendered transparent, as indicated by the dashed outline, to reveal the internal components of the header assembly 110. In an embodiment, the antenna 210 of the header assembly 110 includes the antenna loop 212. As described above, the antenna loop 212 can extend about the longitudinal axis 108 from the first antenna end 260 to the second antenna end 262. More particularly, the antenna loop 212 is an open-loop extending along a transverse plane orthogonal to the longitudinal axis 108 from the first antenna end 260 to the second antenna end 262. The loop can have a circular shape within the transverse plane. The open-loop structure of the antenna 210 can form a monopole antenna. The monopole antenna can be suspended within the header body 802, outside of the metallic portion of the biostimulator 100. More particularly, as described below, the header body 802 can include an insulative material encasing the antenna loop 212. Accordingly, the header body 802 may position, secure, and insulate the antenna 210 distal to the housing 102.

Similar to the antenna loop 212, the fixation element 114 can extend from a first end to a second end. More particularly, the fixation element 114 can extend helically about the longitudinal axis 108 from a proximal end 902 to a distal tip 904. In an embodiment, the header body 802 encases at least a portion of the fixation element 114. For example, the header body 802 can include an insulative material molded around the fixation element 114 to encase the proximal end 902 of the fixation element 114. Accordingly, the header body 802 may position and secure the fixation element 114 distal to the housing 102.

The header body 802 can encase a proximal portion of the fixation element 114 to stabilize and retain the fixation element 114 during delivery into the target tissue. The encased proximal portion of the fixation element 114 may be defined with respect to the turns of the fixation element 114 about the longitudinal axis 108. For example, the proximal portion may have an encased length 906 measured from the proximal end 902 of the fixation element 114 to a point of emergence 908 at which the submerged fixation element 114 becomes exposed above the header body 802. The point of emergence 908 may be a proximalmost location along the fixation element 114 at which at least a portion of a cross-sectional surface area of the fixation element 114 is exposed, e.g., not covered by the header body 802. The encased length 906 may be at least one quarter turn of the helical fixation element 114. Accordingly, a sufficient length and/or volume of fixation element 114 may be held by the header body 802 to ensure that the fixation element 114 is stable and secure.

The header assembly 110 can include electrical components. The antenna 210 may be an electrical component that transmits electrical signals to enable wireless communication. Similarly, the electrode 104 may be integrated in the header assembly 110 and used to communicate pacing signals. The electrical components may be electrically connected to electronic circuitry within the housing 102 via an electrical feedthrough 910.

The electrical feedthrough 910 may be electrically connected to the electronic circuitry within the housing 102. The electronic circuitry can be within the electronics compartment 116 in the housing 102. In an embodiment, the housing 102 has a distal wall 912 separating the electronics compartment 116 from the header assembly 110. For example, the distal wall 912 can extend in a transverse direction to form a closed end to the cylindrical wall containing the electronics compartment 116. The electrical feedthrough 910 can be installed in the distal wall 912. More particularly, the electrical feedthrough 910 can extend through the distal wall 912 of the housing 102. The electrical feedthrough 910 can include feedthrough pins 914 extending longitudinally through a feedthrough insulator 916. The feedthrough pins 914 can connect to the electronic circuitry to convey electrical signals to and from the electrode 104 and/or the antenna 210.

The distal electrode 104 can include an electrode body 606, which is described above, and may have a cup portion and a pin portion. The pin portion can connect to a feedthrough pin 914 to transmit pacing signals through the electrode body 606 to the electrode tip 608. The pins of the electrode 104 and the electrical feedthrough 910 may be mechanically and electrically connected by a joint, such as a weld.

In an embodiment, the distal electrode 104 includes a feature to facilitate engagement with an orientation within the header body 802. For example, the pin portion of the distal electrode 104 may be radially offset from the longitudinal axis 108. By contrast, the cup portion of the distal electrode 104 may be symmetrically disposed about the longitudinal axis 108. Accordingly, when the distal electrode 104 is loaded into a hole formed in the header body 802, the offset pin can engage a corresponding portion of the hole that is radially offset from the portion of the hole that receives the cup. The electrical body may therefore preferentially orient such that the cup and pin engage their respective hole portions. Accordingly, the distal electrode 104 can engage and orient repeatably with respect to the header body 802. The pin portion can align with and connect to a respective feedthrough pin 914.

The antenna 210 may also connect to a respective feedthrough pin 914. In an embodiment, the antenna 210 includes an antenna connector 920 extending from the antenna loop 212. More particularly, the antenna connector 920 can extend from the first antenna end 260 to a connector end 922. The antenna connector 920 may be attached to the feedthrough pin 914 near the connector end 922. For example, the antenna connector 920 may have a J or L shape, and a lower region of the shape can be welded to the feedthrough pin 914. The antenna connector 920 can therefore electrically connect the antenna loop 212 to the electrical feedthrough 910. Accordingly, communication signals may be transferred from the antenna loop 212 to and from the electronic circuitry via the antenna connector 920 and the feedthrough pin 914.

In an embodiment, the header body 802 electrically insulates the other header assembly components. As described below, the header body 802 may be formed from an insulative material, such as a polyether-urethane or an epoxy. The insulative material can be molded, e.g., cast or injected, around the other header assembly components. The header body 802 may therefore separate the components from each other. Furthermore, given the dielectric properties of the insulative material, the header body 802 can electrically isolate the components from each other. The fixation element 114 may therefore be physically separated and electrically decoupled from the antenna 210.

Figure 10:
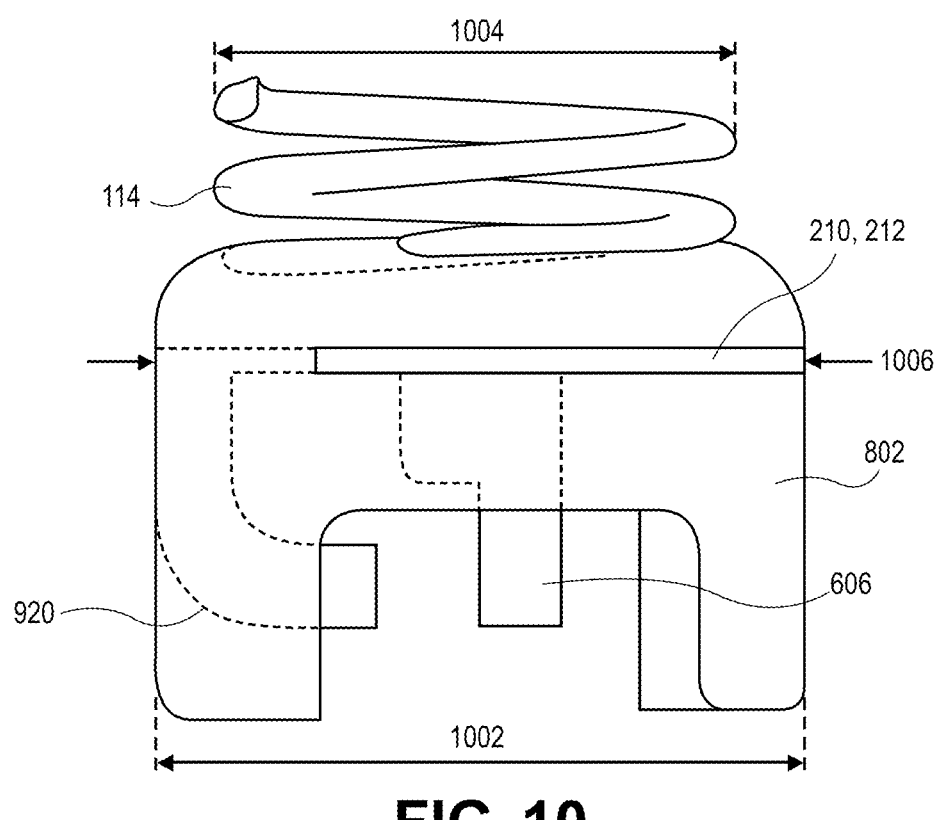
FIG. 10 is a side view of a header assembly, in accordance with an embodiment.

Referring to FIG. 10, a side view of a header assembly is shown in accordance with an embodiment. The omission of the helix mount 112 from the header assembly 110 can allow for a more compact fixation element 114 to be used. More particularly, the header body 802 may have a header diameter 1002 that may be similarly sized to a diameter of the housing 102. A helical diameter 1004 of the fixation element 114, however, may be smaller than the header diameter 1002. The helical diameter 1004 may be an outermost dimension in a transverse direction. For example, the helical diameter 1004 can be a major diameter of the helical wire, or a diameter of an imaginary cylinder containing the helix of the fixation element 114. Embedding the proximal portion of the fixation element 114 directly in the header body 802 allows the fixation element 114 to be secured without threading the helix onto a radially outward surface of the header body 802. Accordingly, the helical diameter 1004 may be less than the dimension of the radially outward surface. A smaller and potentially less traumatic fixation element 114 may therefore be incorporated into the header assembly 110.

Whereas the helical diameter 1004 of the fixation element 114 may be smaller than the header diameter 1002, in an embodiment, a loop diameter 1006 of the antenna loop 212 can be equal to or smaller than the header diameter 1002 of the header body 802. The loop diameter 1006 may be defined as a diameter of the radially outermost surface of the antenna loop 212. The radially outermost surface can be an outward face facing away from the longitudinal axis 108. Accordingly, the radially outermost surface of the antenna loop 212 can be adjacent to or flush with a radially outward surface of the header body 802. Sizing the antenna loop 212 such that the outward surface is adjacent to or flush with the radially outward surface of the header body 802 can allow the antenna 210 to be exposed or nearly exposed to a surrounding environment without extending beyond the radially outward surface. The header assembly can therefore have no sharp edges or protrusions caused by the antenna 210.

In an embodiment, the diameter of the antenna loop 212 is smaller than the header diameter of the header body 802. Sizing the antenna loop 212 to be smaller than the header body 802 can allow for insulative material of the header body 802 to surround the loop. More particularly, the antenna loop 212 can be encapsulated by the insulative material of the header body 802. Accordingly, the insulative material can electrically isolate the antenna loop 212 from the other header components. The insulative material can also cover the antenna loop 212 to physically isolate any edges of the antenna loop 212 from a surrounding environment.

Figure 11:
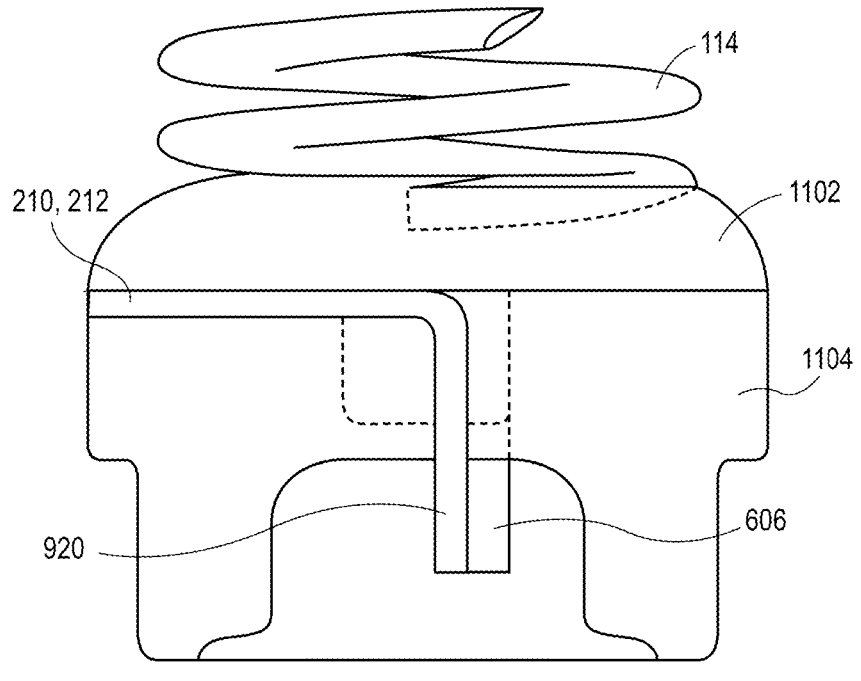
FIG. 11 is a side view of a header assembly, in accordance with an embodiment.

Referring to FIG. 11, a side view of a header assembly is shown in accordance with an embodiment. The header body 802 may be formed from several parts. In an embodiment, the header body 802 includes an intermediary component to provide a seat for both the antenna 210 and the fixation element 114. For example, a header cap 1102 can be formed distal to the antenna loop 212. The header cap 1102 can be a non-metallic component such as a plastic or a ceramic, that conforms to the antenna 210 and the helical element. The header cap 1102 may therefore join the fixation element 114 to the antenna 210 without providing a direct connection, e.g., a weld, between the components. The header cap 1102 can support the other header assembly components. As described below, the header cap 1102 can be formed in a molding process. The molding process may also be used to form a second portion 1104 of the header body 802, proximal to the antenna loop 212, in a same or different casting or injection molding operation. The second portion 1104 of the header body 802 can include holes and/or slots to receive other header assembly components. For example, the second portion 1104 of the header body 802 can include a hole to receive the electrode body 606. Similarly, the antenna connector 920 can pass through a slot in the proximal portion of the header body 802. For example, the J shape of the antenna connector 920 can engage the slot in the molded header body 802 to orient the antenna 210 correctly and to allow the antenna connector 920 to pass through the header body 802 into contact with the feedthrough pin 914. Accordingly, the header body 802 can position and support the fixation element 114, the antenna 210, and the distal electrode 104.

Figure 12:
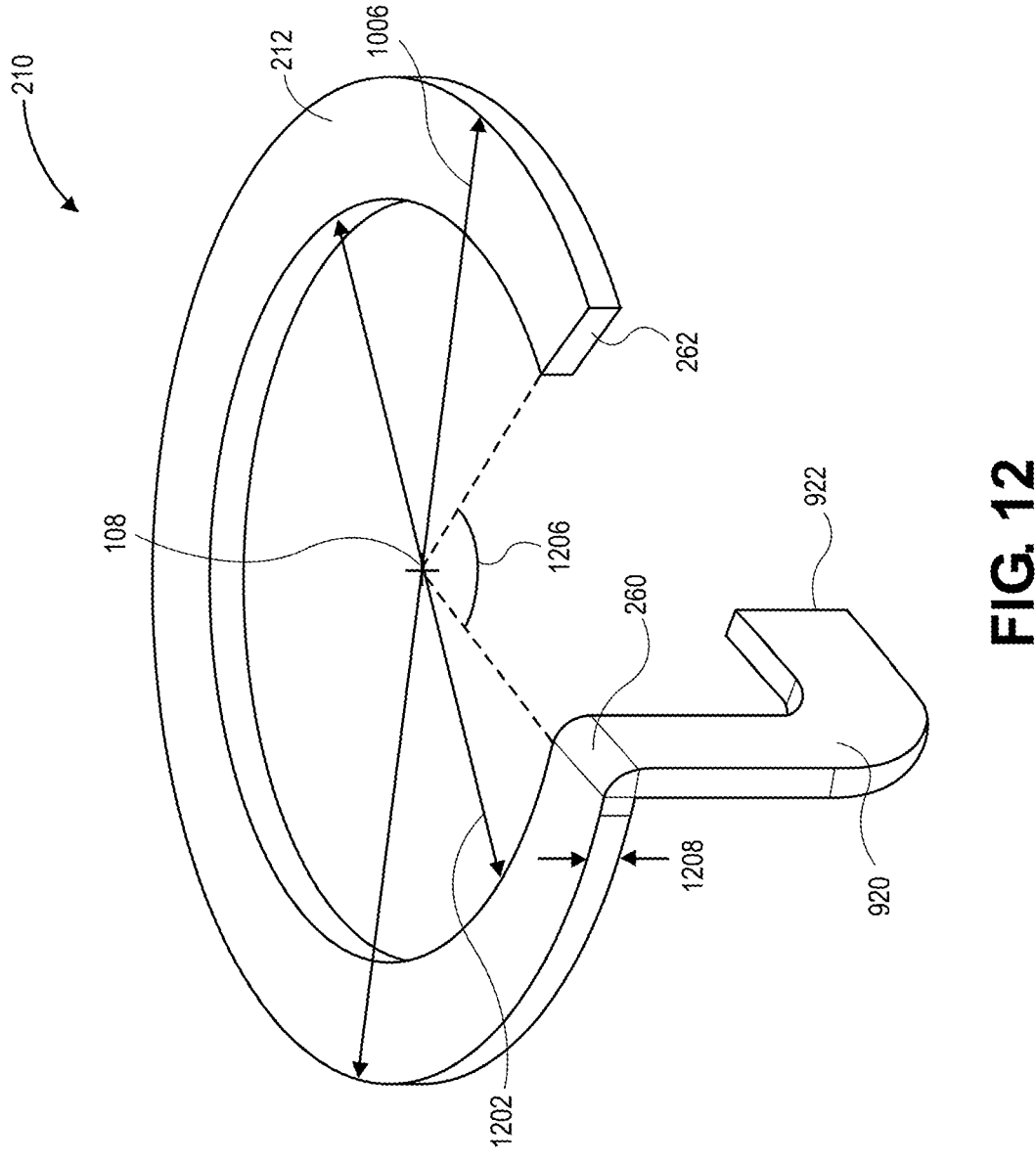
FIG. 12 is a perspective view of an antenna, in accordance with an embodiment.

Referring to FIG. 12, a perspective view of an antenna is shown in accordance with an embodiment. The antenna 210 can include the antenna loop 212 having the circular shape within the transverse plane, and the antenna connector 920 extending downward from the first antenna end 260 to the connector end 922. The antenna loop 212 can be sized to effectively transmit wireless communication signals having a predetermined wavelength. Examples of antenna dimensions useful in transmitting wireless communication signals in the context of a leadless biostimulator 100 are provided below. It will be appreciated, however, that such dimensions and dimensional ranges are provided by way of example, and may be altered.

Dimensions affecting performance of the antenna 210 can include an inner loop diameter 1202 and an outer loop diameter 1006. The diameters can be measured radially relative to the longitudinal axis 108. The inner loop diameter 1202 can be the dimension between the inward facing surface of the open, annular loop. The inner loop diameter 1202 may be in a range of 0.180-0.210 inch, e.g., 0.195 inch. The outer loop diameter 1006 can be the dimension between the outward facing surface at diametrically opposed locations. The outer loop diameter 1006 may be in a range of 0.240-0.275 inch, e.g., 0.257 inch. Another controlled dimension of the antenna loop 212 can be an open angle 1206 measured between the first antenna end 260 and the second antenna end 262. The open angle 1206 can be the angle measured in the circumferential direction about the longitudinal axis 108 between the ends. The open angle 1206 may be in a range of 55°-65°, e.g., 61°. A loop thickness 1208 may also be controlled to achieve a desired antenna performance. The loop thickness 1208 can be a thickness of the ribbon disc forming the antenna loop 212. The loop thickness 1208 (the thickness of the ribbon disc) may be in a range of 0.005-0.010 inch, e.g., 0.008 inch. Accordingly the ribbon disc can have a circumference, length, and or thickness that can be controlled to obtain effective antenna function.

In an embodiment, the antenna 210 can obtain effective antenna function when an antenna length is a quarter or a half of a wavelength of the signal being transmitted. The antenna length can be a length of the antenna loop 212 combined with lengths of connecting structures, such as the lead 314 described above. The connecting structures may alternatively include the antenna connector 920. Accordingly, the antenna length can be a length of the antenna 210 between the connector end 922 and the second antenna end 262, measured along a midline extending from the connector end 922 to the second antenna end 262 between the inner and outer edges of the antenna 210. Furthermore, the connecting structures may also include the feedthrough pin 914. Accordingly, the antenna length can be a length between a proximal end of the feedthrough pin 914 at the housing 102 and the second antenna end 262, measured along the midline.

As described above, the antenna loop 212 can be sized to effectively transmit wireless communication signals having a predetermined wavelength. The predetermined wavelength of the wireless communication signal can be defined as $$\lambda = \frac{distance}{frequency}.$$

In an embodiment, and by way of example only, the predetermined wavelength is 12.4 cm, corresponding to a wireless communication signal frequency of 2.4 GHz. More particularly, the antenna 210 can be configured to transmit a wireless communication signal having a frequency of 2.4 GHz. Accordingly, the antenna 210 can have a minimum antenna length, e.g., measured from the proximal end of the feedthrough pin 914 to the second antenna end 262, of 3.1 cm $$\left(1/4\lambda = 1/4 \times \frac{3 * 10^8 \text{ m/s}}{2.4 \text{ GHz}}\right).$$

Figure 13:
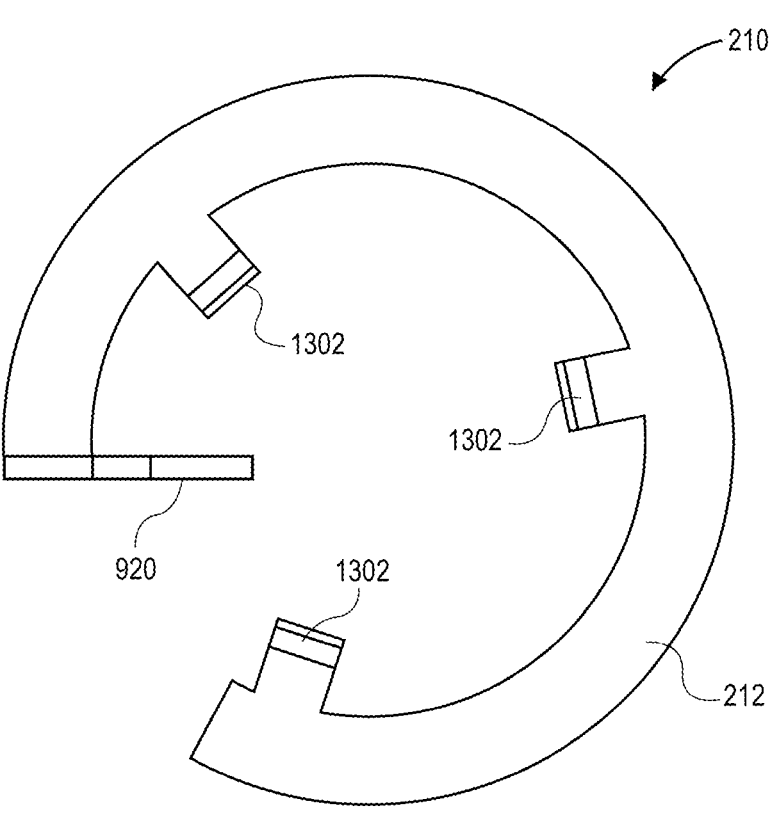
FIG. 13 is a top view of an antenna, in accordance with an embodiment.

Referring to FIG. 13, a top view of an antenna is shown in accordance with an embodiment. Optionally, the antenna 210 may include features to enhance mechanical bonding between the antenna loop 212 and the surrounding material of the header body 802. For example, the antenna 210 may include one or more prongs 1302 extending outward from the antenna loop 212. The prongs 1302 may be protrusions, tabs, or other projecting structures that can increase an out-of-plane volume of the antenna 210. Accordingly, the header body 802, which surrounds the prongs 1302 and the antenna loop 212, can interfere with and grip the prongs 1302 to mechanically engage and secure the antenna loop 212 within the header assembly 110.

Figure 14:
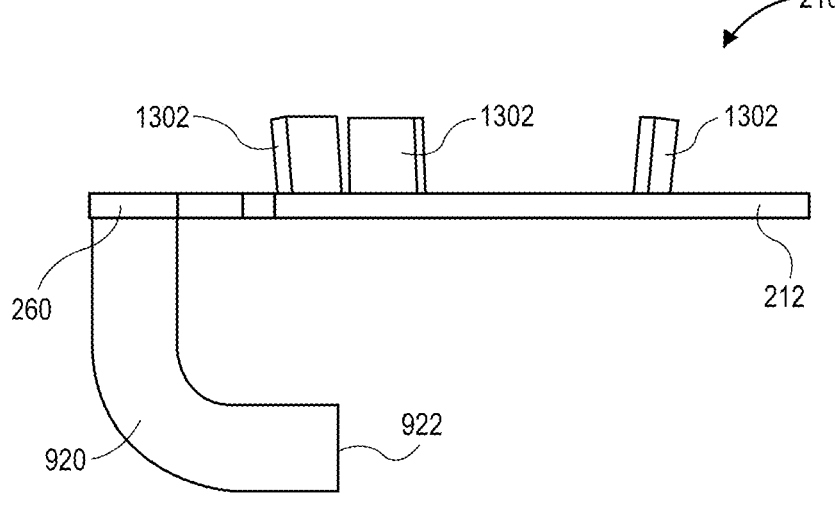
FIG. 14 is a side view of an antenna, in accordance with an embodiment.

Referring to FIG. 14, a side view of an antenna is shown in accordance with an embodiment. In the side view, the prongs 1302 are shown projecting upward, out of the transverse plane within which the antenna loop 212 extends. The prongs 1302 can engage the surrounding insulative material, which may be flowed or injected around the prongs 1302 during a method of manufacturing, as described below.

In the side view, a profile of the antenna connector 920 is shown. The profile may be a J shape. More particularly, the antenna connector 920 can include a first, downward extending portion. The downward extending portion can extend from the first antenna end 260. The antenna connector 920 may also include an inward extending portion. The inward extending portion can extend radially inward from the downward extending portion to the connector end 922. The connector end 922 may be radially inward from the first antenna end 260. Accordingly, the connector end 922 may be attached to the electrical feedthrough 910 that is centrally located.

The antenna connector 920 may be integrally formed with the antenna loop 212, as shown. Alternatively, the antenna connector 920 may be a separate component. For example, the antenna connector can be a conductive connector, such as a wire or a flexible cable, that connects to the first antenna end 260 at a first end and to the electrical feedthrough 910 at a second end.

Figure 15:
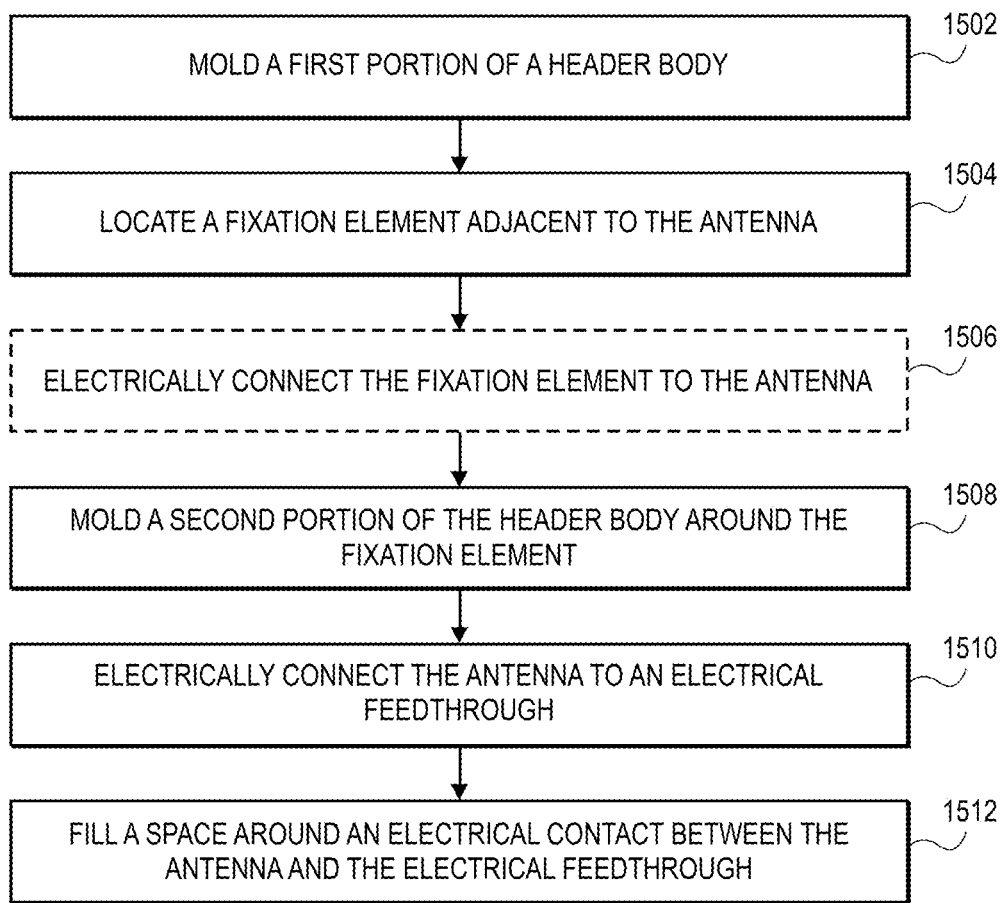
FIG. 15 is a flowchart of a method of manufacturing a header assembly, in accordance with an embodiment.

Referring to FIG. 15, a flowchart of a method of manufacturing a header assembly is shown in accordance with an embodiment. Illustrations of the header assembly 110 at each operation of the method are shown in FIGS. 16A-16F.

Figures 16A, 16B:
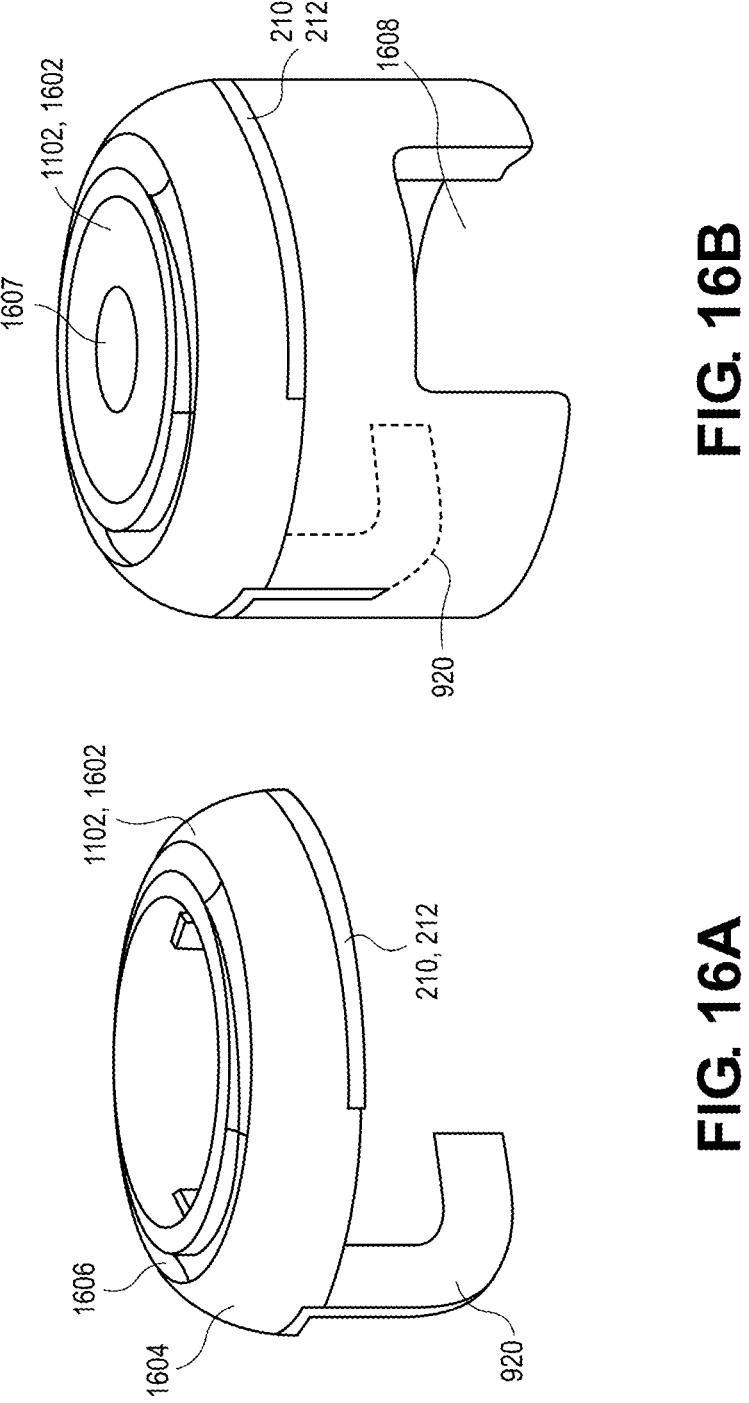
FIGS. 16A-16F are perspective views illustrating operations of a method of manufacturing a header assembly, in accordance with an embodiment.
Figure 16D:
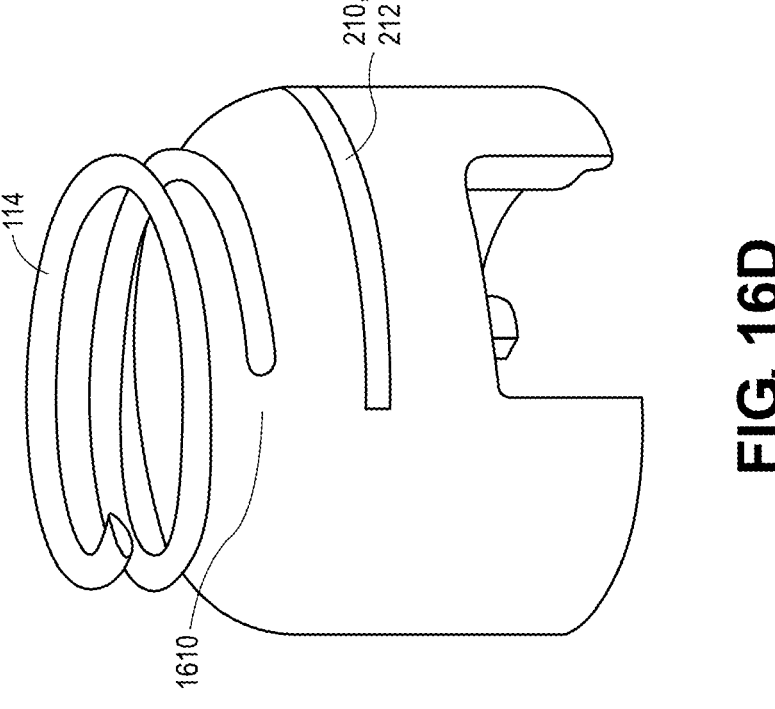
Figure 16C:
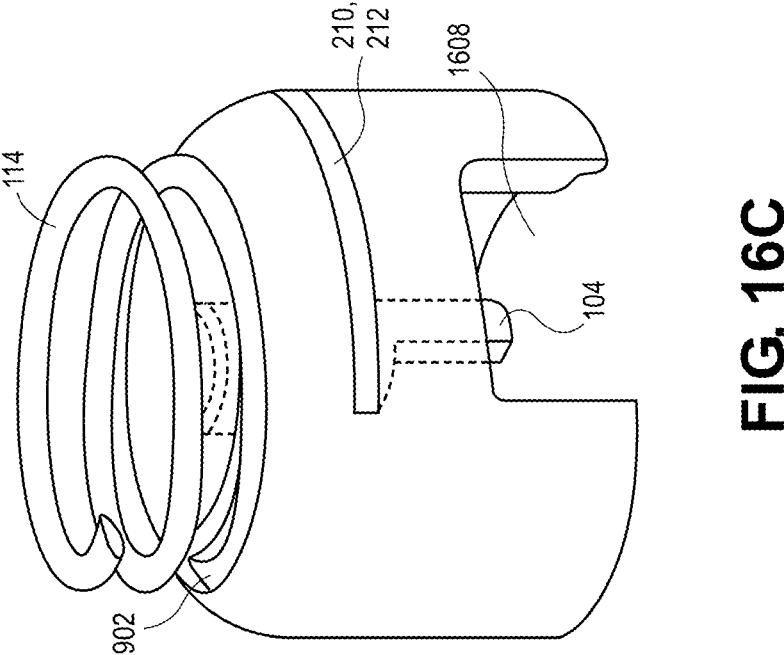
Figure 16F:
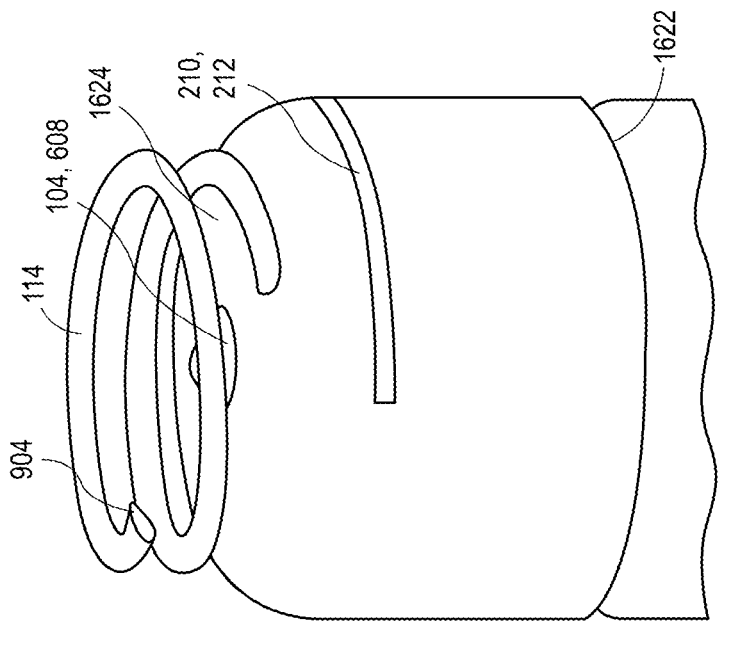

Accordingly, FIGS. 15-16F are alternately referred to below. The operations shown and described below can be used to fabricate the header assembly 110 having the header body 802 surrounding and/or encasing the fixation element 114 and the antenna 210. The operations may, however, be carried out in a different sequence than described. Furthermore, operations may be added or removed. Accordingly, the method of manufacturing is provided by way of illustration and not limitation.

Referring to FIG. 16A, a perspective view illustrating operations of a method of manufacturing a header assembly is shown in accordance with an embodiment. At operation 1502, a first portion 1602 of the header body 802 is molded. The first portion 1602 can be molded around the antenna 210. The header body 802 may be formed using one or more insulative materials. For example, the first portion 1602 of the header body 802 may be molded from a polyether-urethane or an epoxy. The first portion 1602 may include the header cap 1102 of the header body 802.

The header cap 1102 can be molded directly onto the antenna 210 or, alternatively, may be a pre-molded part onto which the antenna 210 is mounted. For example, the header cap 1102 can be a pre-molded part having several features to receive and/or orient the fixation element 114 in a particular manner relative to the antenna 210. In an embodiment, the first portion 1602 can function as an anchor 1604. The header cap 1102 can include the anchor 1604 to connect the fixation element 114 to the antenna 210. The antenna 210 may, for example, fit onto a bottom face of the anchor 1604. The bottom face can have a receiving slot shaped to conform to the antenna loop 212 and/or the prongs 1302. Accordingly, the antenna 210 can fit snugly against and engage the anchor 1604. Similarly, the anchor 1604 can include a slot 1606 to receive the fixation element 114, as described below.

Referring to FIG. 16B, a perspective view illustrating operations of a method of manufacturing a header assembly is shown in accordance with an embodiment. The first portion 1602 of the header body 802 may be completed after engaging the antenna 210 to the header cap 1102. More particularly, a multipass molding process may be used to add additional insulative material. The additional insulative material may form the portion of the header body 802 below the antenna 210. Furthermore, the additional insulative material can fill a central space 1608 within the header cap 1102. The central filling can define a central hole 1607 to receive the electrode cup. Furthermore, the filling can surround a space 1608 within which the antenna connector 920 can extend. More particularly, the space 1608 may be used to receive the electrical feedthrough 910 to make electrical connections between the antenna connector 920 and the feedthrough pins 914.

Referring to FIG. 16C, a perspective view illustrating operations of a method of manufacturing a header assembly is shown in accordance with an embodiment. At operation 1504, the fixation element 114 may be located adjacent to the antenna 210. The slot 1606 may be along a distally-facing surface of the anchor 1604. The slot 1606 can have a shape that conforms to the proximal portion of the fixation element 114 that will be embedded within the header body 802. More particularly, the slot 1606 can have a diameter matching the helical diameter 1004, and the slot 1606 can be recessed into the distally-facing surface to a depth that is equal to or greater than a diameter of the wire used to form the helical fixation element 114. Accordingly, the proximal end 902 of the fixation element 114 can be inserted into the slot 1606. When placed in the slot 1606, the proximal end 902 can be adjacent to the antenna 210. More particularly, the fixation element 114 can be positioned adjacent to the antenna 210. The anchor 1604 can therefore physically connect the antenna 210 to the fixation element 114 in a predetermined position. It will be appreciated, however, that the anchor 1604 may be formed from the insulative material, and thus, can electrically insulate the fixation element 114 from the antenna 210. Accordingly, the fixation element 114 may not, in an embodiment, affect the function of the antenna 210.

In addition to installing the fixation element 114, the distal electrode 104 may also be installed in the header body 802. The distal electrode 104 is primarily hidden by the header body 802 in FIG. 16C, as indicated by dashed lines. It will be appreciated, however, that the electrode cup may be positioned within the central hole 1607 of the first portion 1602 of the header body 802. Furthermore, the pin portion of the electrode 104 can extend downward into the space 1608. Accordingly, the distal electrode 104 may be appropriately located for connection to the electrical feedthrough 910.

Optionally, at operation 1506, the fixation element 114 is electrically connected to the antenna 210. Such operation is not illustrated in FIGS. 16A-16F. The operation is, however, described below with respect to FIG. 21C. Nonetheless, the operation is mentioned here to underscore the interchangeability of manufacturing operations to fabricate the various header assembly embodiments described herein.

Referring to FIG. 16D, a perspective view illustrating operations of a method of manufacturing a header assembly is shown in accordance with an embodiment. At operation 1508, a second portion 1610 of the header body 802 is molded around the fixation element 114. For example, the second portion 1610 may be molded around a proximal portion of the fixation element 114, e.g., surrounding the proximal end 902 of the fixation element. The second portion 1610 may be formed from a same or different insulative material than the insulative material used to form the first portion 1602 of the header body 802. The second portion 1610 can conform to and merge with the first portion 1602. For example, the second portion 1610 may fill the slot 1606 around the fixation element 114. More particularly, the second portion 1610 may cover the fixation element 114 that is received within the slot 1606. The covering can secure fixation element 114. The covering may also form an atraumatic, smooth surface over the header body 802. Accordingly, the molding pass can provide a subassembly in which the fixation element 114 is securely positioned relative to the antenna 210.

Figure 16E:
Figure 16E:
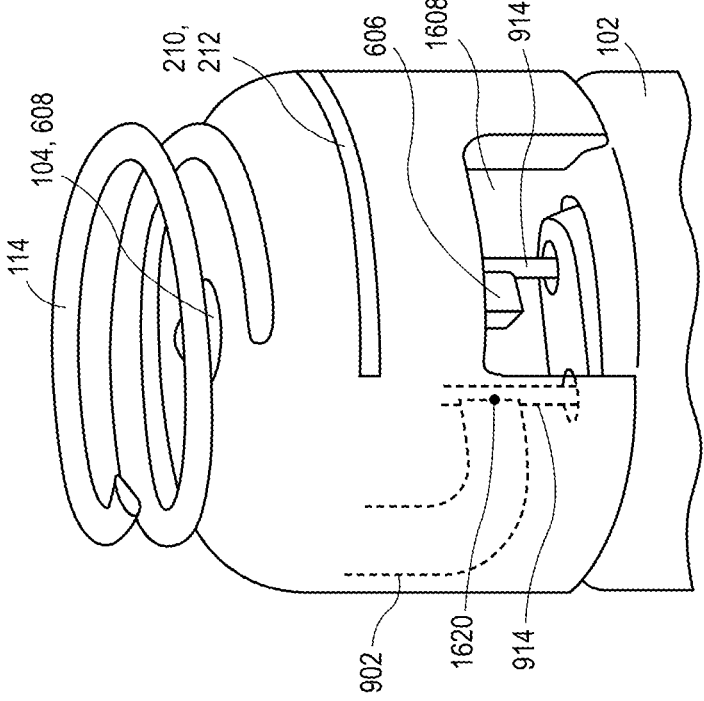

Referring to FIG. 16E, a perspective view illustrating operations of a method of manufacturing a header assembly is shown in accordance with an embodiment. At operation 1510, the antenna 210 is electrically connected to the electrical feedthrough 910, which extends through the housing 102. The header subassembly described above can be fit on top of the housing 102. When mounted on the housing 102, the feedthrough pins 914 of the electrical feedthrough 910 can extend upward into the space 1608. For example, a first feedthrough pin 914 can extend upward to a location adjacent to the antenna connector 920, and a second feedthrough pin 914 can extend upward to a location adjacent to electrode body 606.

Electrical connections can be made between the feedthrough pins 914 and the respective header assembly components. The electrode body 606 can be mechanically and electrically connected to the respective feedthrough pin 914 by a first weld. Similarly, the antenna connector 920 may be welded to the respective feedthrough pin 914 at an electrical contact 1620 between the components. Accordingly both the antenna 210 and the distal electrode 104 may be electrically connected to the electronic circuitry through the electrical feedthrough 910.

Referring to FIG. 16F, a perspective view illustrating operations of a method of manufacturing a header assembly is shown in accordance with an embodiment. At operation 1512, the space 1608 around the electrical contact 1620 is filled. For example, an epoxy or another insulative material may be flowed into the space 1608 to backfill the space. The backfill can surround and electrically isolate the electrical connections between the header assembly components and the electrical feedthrough 910. In an embodiment, the filler can merge with the previously molded portions of the header body 802, e.g., to form a singular header body. A monolithic header body 802 may therefore be formed by the several molding and backfill operations. More particularly, the finished header body 802 can have a smooth, continuous outer surface extending from a proximal header end 1622 to a distal header end 1624. The distal header end 1624 may be at a location surrounding the electrode tip 608. The fixation element 114 can emerge from within the header body 802 and extend to the distal tip 904. The finished header assembly 110 can therefore provide a compact, atraumatic form factor that facilitates attachment to target tissue by the fixation element 114 and facilitates wireless communication of data by the antenna 210.

Figure 17:
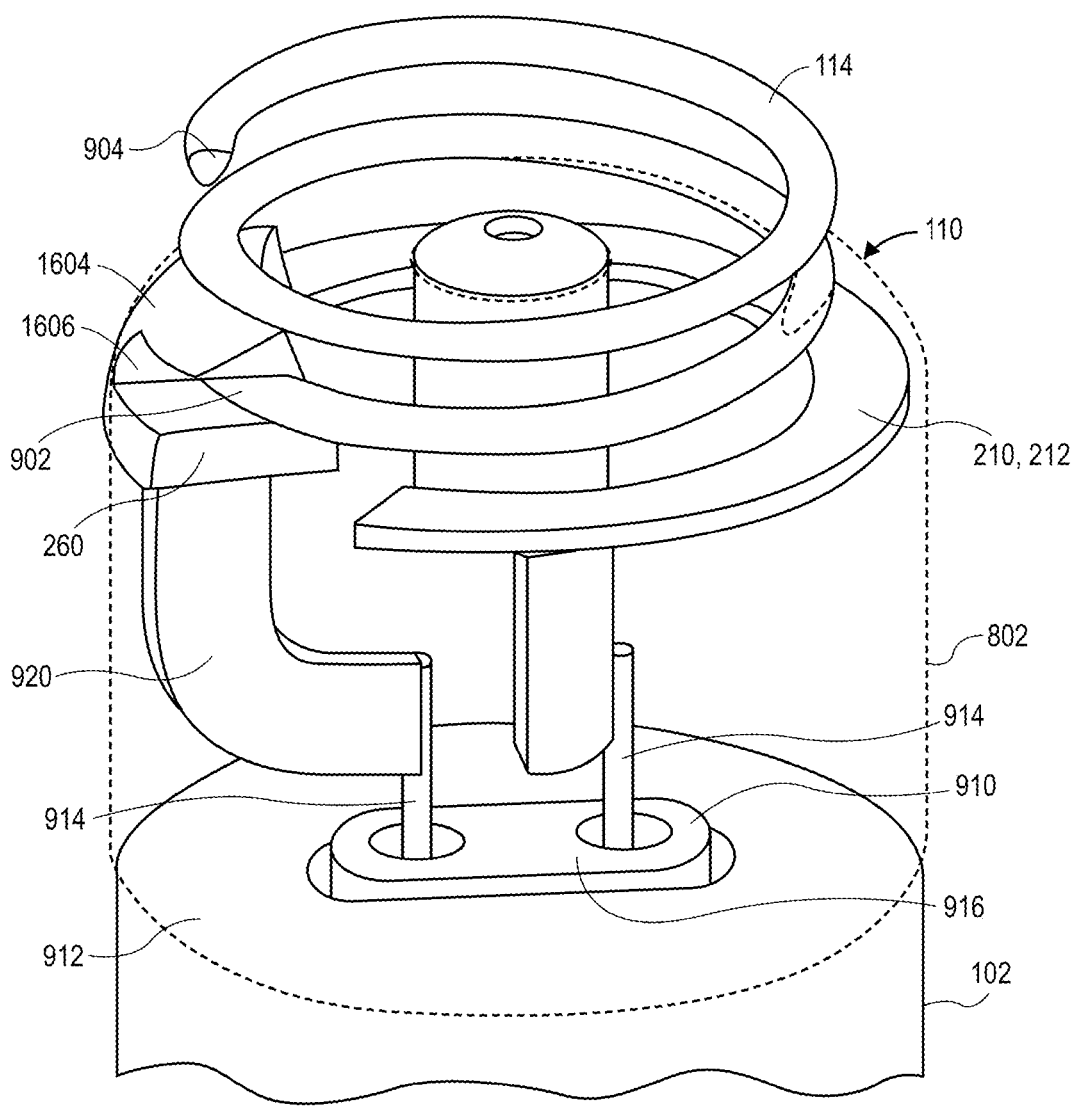
FIG. 17 is a perspective view of a header assembly, in accordance with an embodiment.

Referring to FIG. 17, a perspective view of a header assembly is shown in accordance with an embodiment. In an embodiment, the fixation element 114 may be used as an extension of the antenna 210. The fixation element 114 and the antenna 210 may be fused within the header body 802, which is rendered transparent as indicated by the dashed lines. For example, the antenna 210 may include the anchor 1604, which in an embodiment is a volume of material at the first antenna end 260. The bulk of material may be located at the first antenna end 260 between the antenna loop 212 and the antenna connector 920. The anchor 1604 may be a portion of the antenna 210, and thus, may be formed from a same metallic or conductive material that the antenna loop 212 and the antenna connector 920 are formed from. The anchor 1604 can electrically connect the antenna loop 212 to the antenna connector 920.

The anchor 1604 can electrically connect the fixation element 114 to the antenna 210. In an embodiment, the anchor 1604 includes the slot 1606 to receive the proximal end 902 of the fixation element 114. The slot 1606 may therefore be formed in the anchor 1604 portion of the antenna 210, rather than being formed in the header cap 1102 as described above. When the proximal end 902 of the fixation element 114 is inserted into the slot 1606, the fixation element 114 can be mechanically and electrically connected to the antenna 210.

When the antenna 210 is welded to the fixation element 114, an effective length of the antenna 210 can be increased. More particularly, the combined antenna structure can have increased surface area for wireless signal capture. Attaching the helix of the fixation element 114 to the antenna 210 creates a compound antenna 210. The compound antenna 210 can include a monopole portion of the antenna and a helical portion of the antenna. Those portions are merged into one. The wireless signal from an external transmitter may propagate through the several antenna structures as it radiates outside of the biostimulator 100. The net effect can be that the compound antenna 210 is able to have improved antenna gain and radiation pattern when compared to a monopole antenna alone. The addition of material to the antenna 210 through the attachment to the fixation element 114 can also add inductance to the antenna structure. Increased inductance can improve the antenna 210 impedance, thereby improving signal transfer from the electronic circuitry to the antenna 210. Test data proves that the imaginary portion of impedance is reduced substantially by the two-component antenna 210 operating at 2.45 GHz. More particularly, it has been shown that the addition of the fixation element 114 to the antenna structure improves antenna function.

In addition to improved antenna function, attaching the fixation element 114 to the antenna 210 can enhance mechanical integrity of the header assembly 110. Welding the fixation element 114 to antenna 210 can provide a mechanical attachment between the components that reduces the likelihood of the fixation element 114 detaching from the biostimulator 100. More particularly, a mechanical bond between the fixation element 114 and the anchor 1604 or antenna loop 212 can reduce the likelihood that the fixation element 114 will dislodge from the header assembly 110 during use.

Figure 18:
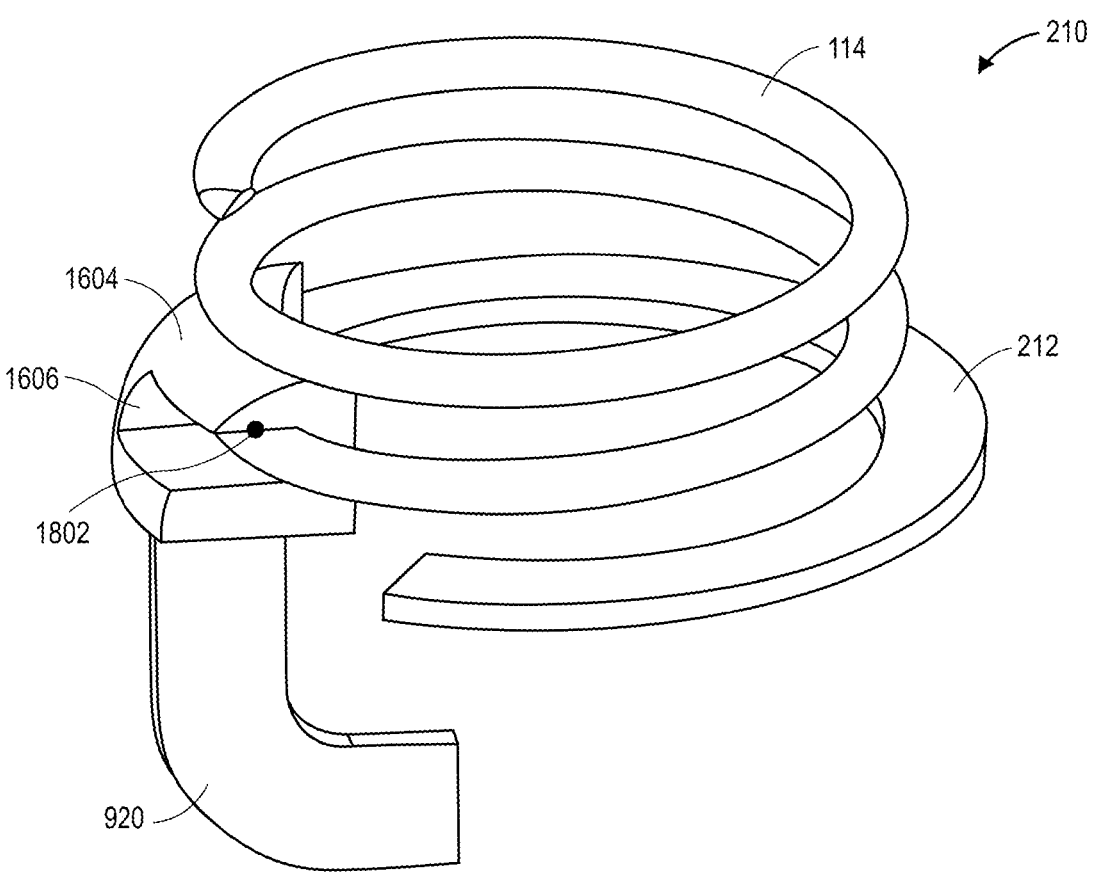
FIG. 18 is a perspective view of an antenna, in accordance with an embodiment.

Referring to FIG. 18, a perspective view of an antenna is shown in accordance with an embodiment. The several components of the antenna 210 may be joined by welding the components together. More particularly, the antenna 210 can include a weld joint 1802 between the anchor 1604 and the fixation element 114. The anchor 1604 can be a portion of the antenna 210, and thus, the weld joint 1802 can electrically connect the fixation element 114 to the antenna 210 through the anchor 1604.

Figure 19:
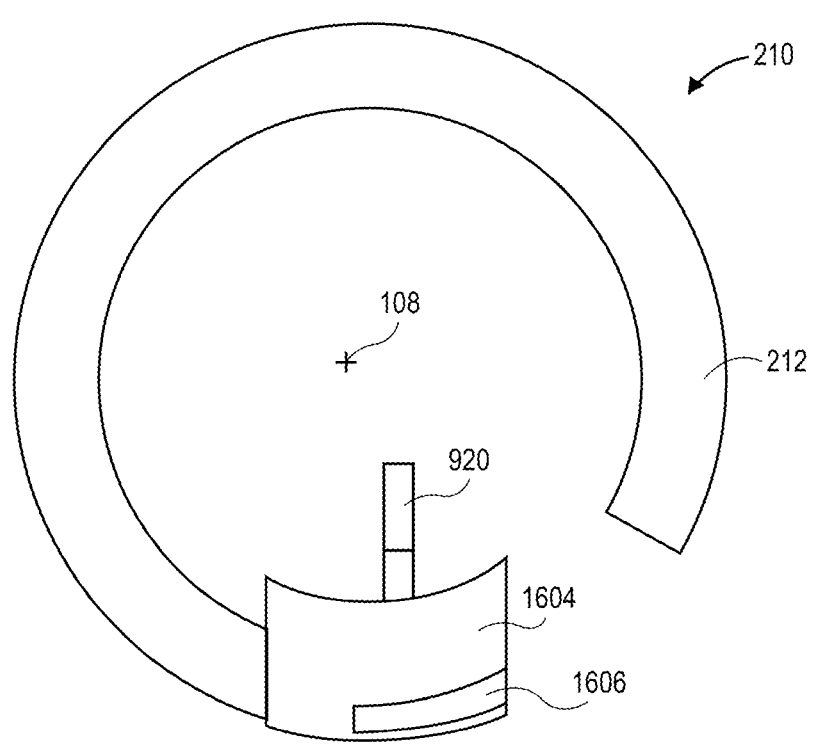
FIG. 19 is a top view of an antenna, in accordance with an embodiment.

Referring to FIG. 19, a top view of an antenna is shown in accordance with an embodiment. The dimensions of the antenna 210 having the anchor 1604 may be similar to those described above. The fixation element 114 is removed from the antenna 210 in FIG. 19; however, it will be appreciated that the slot 1606 within which the fixation element 114 is received has a radially inward surface that is closer to the longitudinal axis 108 than the outward facing surface of the antenna loop 212. Accordingly, the relative diameters of the antenna loop 212, the fixation element 114, and the header body 802 may be similar to those described above.

Figure 20:
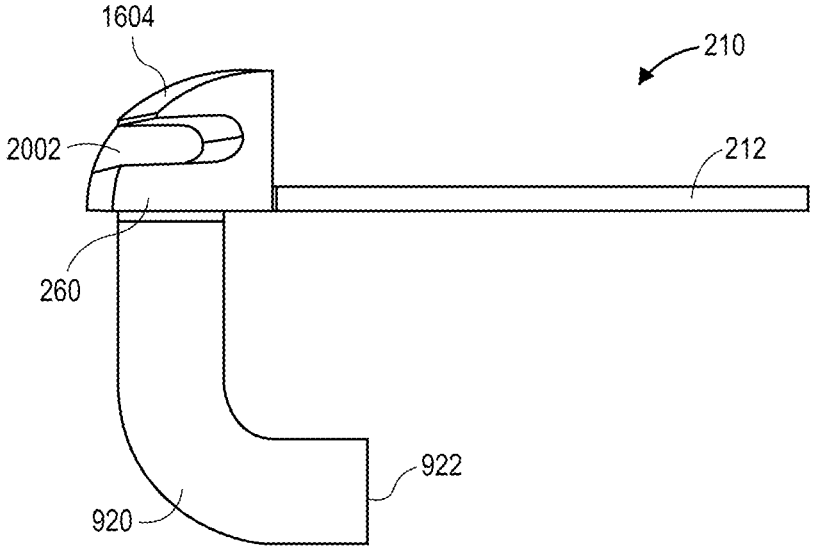
FIG. 20 is a side view of an antenna, in accordance with an embodiment.

Referring to FIG. 20, a side view of an antenna is shown in accordance with an embodiment. The anchor 1604 can include a stop surface 2002. The stop surface 2002 may be a surface against which the proximal end 902 of the fixation element 114 is positioned when joining the components together. More particularly, by placing the proximal end 902 of the fixation element 114 at the stop surface 2002, an orientation of the fixation element 114, e.g., the distal tip 904, relative to the antenna loop 212 and the device housing 102 may be repeatably set. Accordingly, the anchor 1604 can promote mechanical and electrical connection between the fixation element 114 and the antenna 210, and can also enhance manufacturability of the biostimulator 100.

Referring again to FIG. 15, the previously described operations may be used to form the header assembly 110 having the compound antenna. Illustrations of the header assembly 110 at each operation of the method are shown in FIGS. 21A-21F. Accordingly, FIGS. 15 and 21A-21F are alternately referred to below. The operations shown and described below can be used to fabricate the header assembly 110 having the header body 802 surrounding and/or encasing the combined antenna/fixation element structure. The operations may, however, be carried out in a different sequence than described. Furthermore, operations may be added or removed. Accordingly, the method of manufacturing is provided by way of illustration and not limitation.

Figures 21A, 21B:
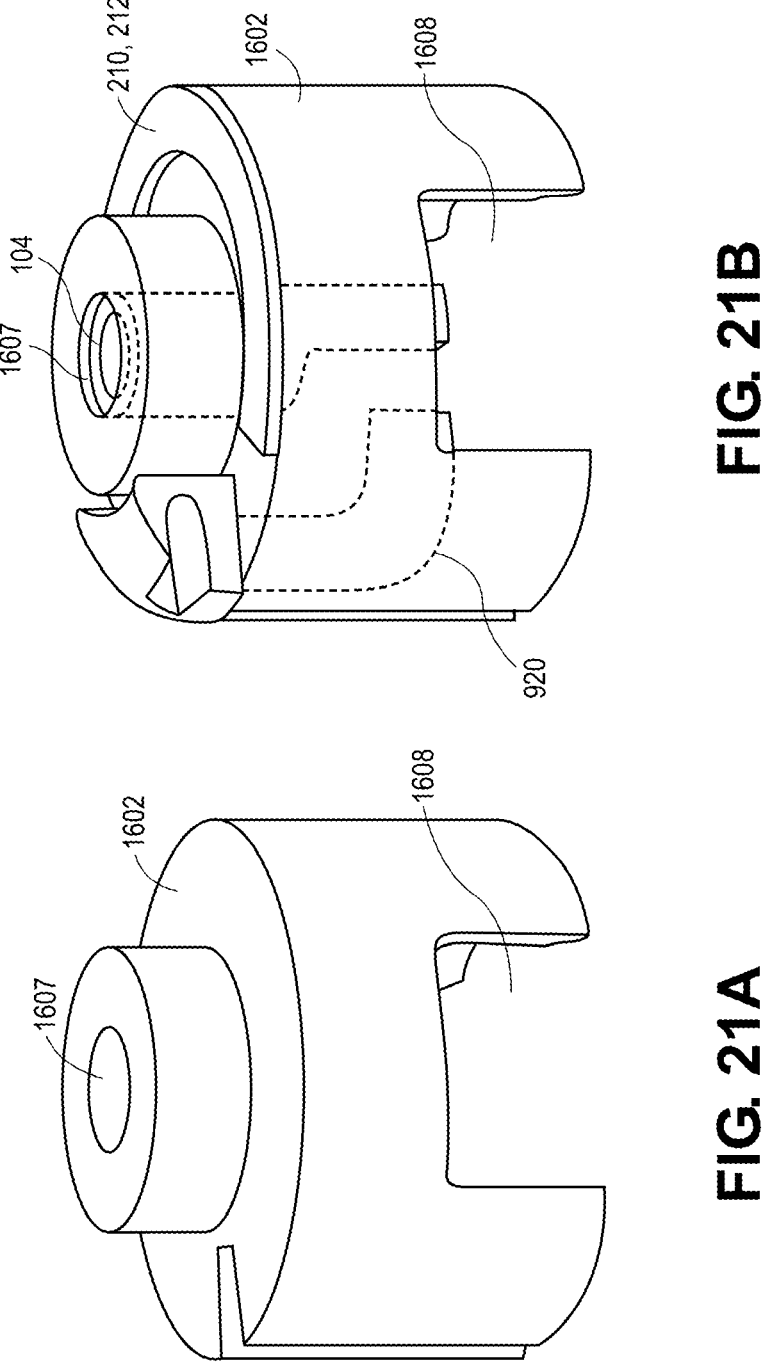
FIGS. 21A-21F are perspective views illustrating operations of a method of manufacturing a header assembly, in accordance with an embodiment.

Referring to FIG. 21A, a perspective view illustrating operations of a method of manufacturing a header assembly is shown in accordance with an embodiment. Several molding operations may be used to form the header body 802, as described above. The operations can be performed in one or more passes of liquid deposition of the insulative material (s). More particularly, the insulative materials may be additively applied to build up the finished header body 802.

At operation 1502, a first portion 1602 of a header body 802 is formed. The first portion 1602 can include a base body having features to receive other header assembly components. For example, the first portion 1602 can include the central hole 1607 to receive the distal electrode 104. The first portion 1602 can also include a channel along a lateral side to receive the antenna connector 920.

Referring to FIG. 21B, a perspective view illustrating operations of a method of manufacturing a header assembly is shown in accordance with an embodiment. The antenna 210 and the distal electrode 104 may be placed into the respective receiving structures of the first portion 1602 of the header body 802. The antenna connector 920 can be inserted into the channel along the side of the header body 802 to extend downward through the first portion 1602 into the space 1608. The distal electrode 104 may be inserted into the central hole 1607 such that the electrode pin extends downward into the space 1608.

Figure 21D:
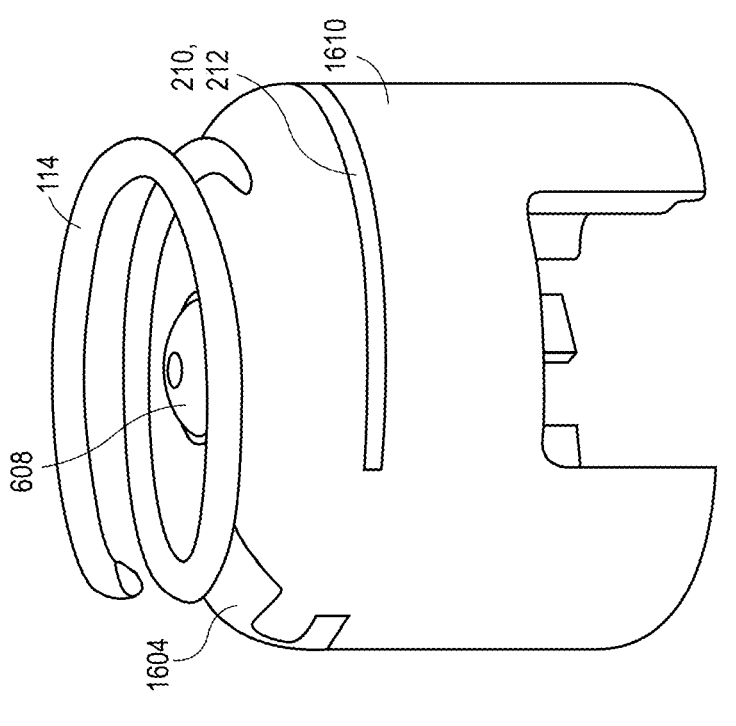
Figure 21C:
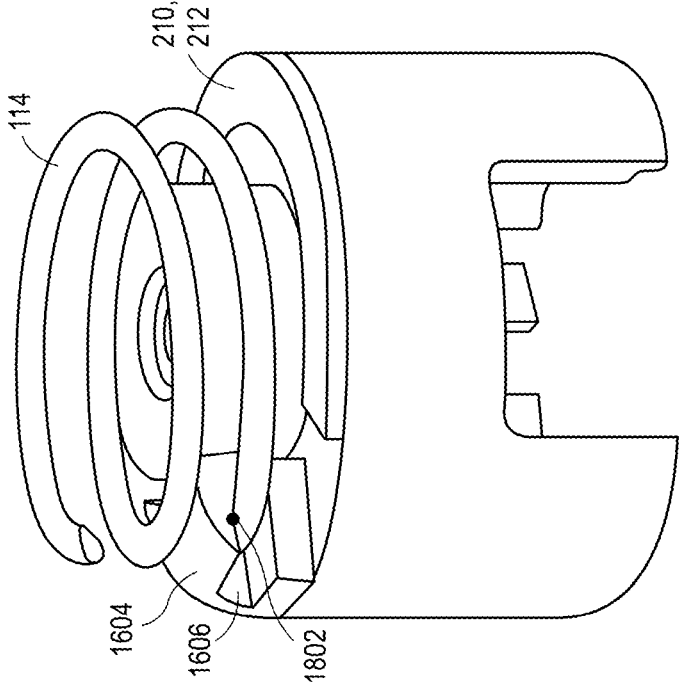

Referring to FIG. 21C, a perspective view illustrating operations of a method of manufacturing a header assembly is shown in accordance with an embodiment. At operation 1504, the fixation element 114 can be located adjacent to the antenna 210. More particularly, the proximal portion of the fixation element 114 can be inserted into the slot 1606 of the anchor 1604. When inserted into the slot 1606, the fixation element 114 may be immediately adjacent to and in contact with the antenna 210.

At operation 1506, which was described as optional above, the fixation element 114 may be electrically connected to the antenna 210. The electrical connection may be formed by welding the components together at the weld joint 1802. When welded together, the compound antenna structure is formed. The compound antenna 210 can have enhanced performance characteristics, as described above.

Referring to FIG. 21D, a perspective view illustrating operations of a method of manufacturing a header assembly is shown in accordance with an embodiment. At operation 1508, the second portion 1610 of the header body 802 can be molded around the proximal end 902 of the fixation element 114. The second portion 1610 can be deposited in a molding pass that flows the insulative material into the slot 1606 of the anchor 1604. The insulative material may also fill in around the anchor 1604 and the antenna loop 212 to provide a continuous, smooth distal end of the header body 802.

Figure 21F:
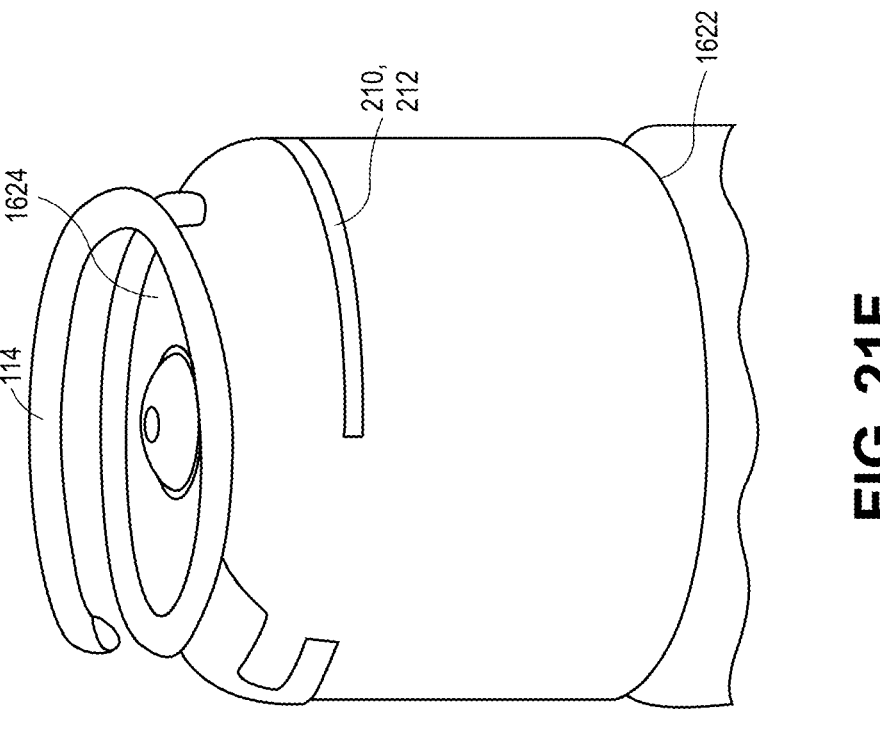
Figure 21E:
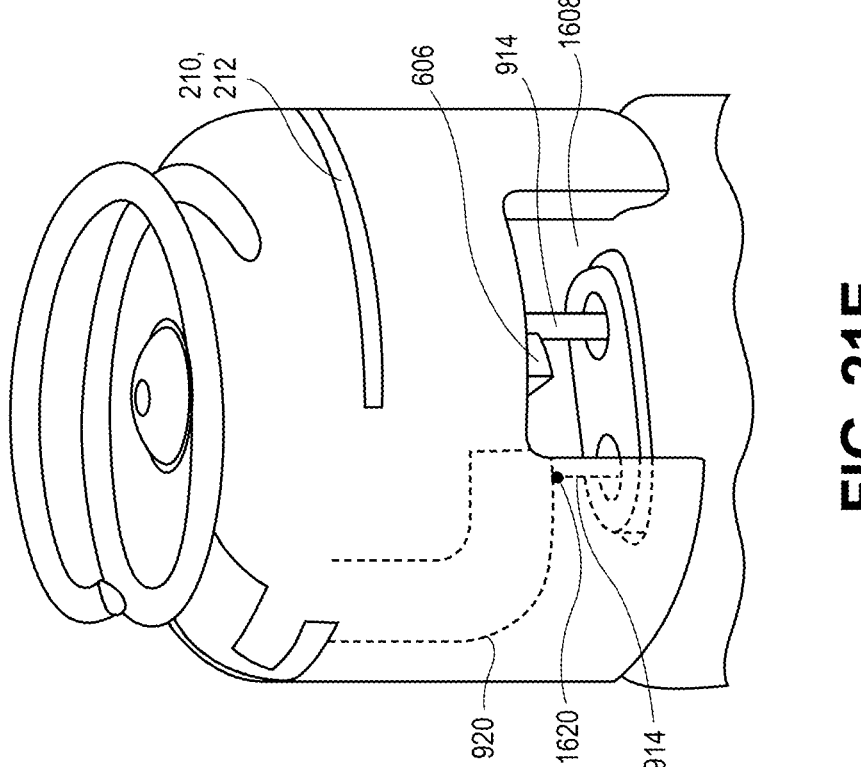

Referring to FIG. 21E, a perspective view illustrating operations of a method of manufacturing a header assembly is shown in accordance with an embodiment. At operation 1510, as described above, electrical connections can be made between the antenna 210 and the electrical feedthrough 910. Electrical connection may also be formed between the electrode body 606 and the electrical feedthrough 910. The welds that form the electrical connections can be made after mounting the molded header body 802 on the device housing 102. Alternatively, the electrical connections may be made prior to the molding operations described above. For example, electrical connections can be made between the electrical feedthrough 910 and the antenna and electrode structures prior to performing the molding passes.

The electrical components may first be bonded together and suspended by the electrical feedthrough 910 relative to the device housing 102. The various molding operations may then be performed to deposit insulative material around the electrical components. Accordingly, the operations of the methods described above may be performed in various sequences.

Referring to FIG. 21F, a perspective view illustrating operations of a method of manufacturing a header assembly is shown in accordance with an embodiment. At operation 1512, the space 1608 around the electrical contact 1620 may be filled. The backfilling operation, as described above with respect to FIG. 16F, can result in a finished header having a smooth continuous surface between the header ends. The biostimulator 100 having the antenna 210 and fixation element 114 at least partially encased within the header body 802 may therefore be provided.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A header assembly for a biostimulator, comprising:
an antenna including an antenna loop extending about a longitudinal axis;
a fixation element located adjacent to the antenna and extending helically about the longitudinal axis from a proximal end to a distal tip; and
a header body including an insulative material encasing the antenna loop and the proximal end of the fixation element.

2. The header assembly of claim 1 further comprising an anchor connecting the fixation element to the antenna.

3. The header assembly of claim 2, wherein the anchor includes a slot to receive the proximal end of the fixation element.

4. The header assembly of claim 2, wherein the anchor electrically insulates the fixation element from the antenna.

5. The header assembly of claim 2, wherein the anchor electrically connects the fixation element to the antenna.

6. The header assembly of claim 1, wherein the antenna loop is an open loop extending along a transverse plane orthogonal to the longitudinal axis from a first antenna end to a second antenna end.

7. The header assembly of claim 1 further comprising one or more prongs extending outward from the antenna loop.

8. The header assembly of claim 1, wherein a helical diameter of the fixation element is smaller than a header diameter of the header body.

9. The header assembly of claim 1, wherein a loop diameter of the antenna loop is equal to or smaller than a header diameter of the header body.

10. A method, comprising:
molding one or more insulative materials into a first portion of a header body around an antenna;
locating a proximal end of a fixation element adjacent to the antenna; and
molding the one or more insulative materials into a second portion of the header body around the proximal end of the fixation element.

11. The method of claim 10 further comprising electrically connecting the fixation element to the antenna.

12. The method of claim 10 further comprising electrically connecting the antenna to an electrical feedthrough extending through a housing, wherein the housing includes an electronics compartment containing electronic circuitry electrically connected to the electrical feedthrough.

\* \* \* \* \*